(12) United States Patent
Sorge et al.

(10) Patent No.: US 7,517,688 B2
(45) Date of Patent: Apr. 14, 2009

(54) METHOD FOR LIGATING NUCLEIC ACIDS AND MOLECULAR CLONING

(75) Inventors: Joseph A. Sorge, Del Mar, CA (US); Carsten-Peter Carstens, San Diego, CA (US)

(73) Assignee: Stratagene California, La Jolla, CA (US)

( * ) Notice: Subject to any disclaimer, the term of this patent is extended or adjusted under 35 U.S.C. 154(b) by 335 days.

(21) Appl. No.: 11/284,343

(22) Filed: Nov. 21, 2005

(65) Prior Publication Data

US 2006/0166332 A1 Jul. 27, 2006

Related U.S. Application Data

(63) Continuation-in-part of application No. 10/057,050, filed on Jan. 25, 2002, now Pat. No. 7,109,178, which is a continuation of application No. 09/513,710, filed on Feb. 25, 2000, now abandoned.

(51) Int. Cl.
*C12N 15/87* (2006.01)
(52) U.S. Cl. ................ 435/462; 435/252.33; 435/91.41
(58) Field of Classification Search ....................... None
See application file for complete search history.

(56) References Cited

U.S. PATENT DOCUMENTS

| | | | | |
|---|---|---|---|---|
| 4,959,317 | A | 9/1990 | Sauer | 435/462 |
| 5,731,182 | A | 3/1998 | Boyce | 435/183 |
| 5,763,240 | A | 6/1998 | Zarling et al. | 435/172.3 |
| 5,766,891 | A | 6/1998 | Shuman | 435/91.41 |
| 5,888,732 | A | 3/1999 | Hartley et al. | 435/6 |
| 6,087,170 | A | 7/2000 | Kemble | 435/368 |
| 6,376,192 | B1 | 4/2002 | Elledge et al. | 435/6 |
| 2003/0224521 | A1* | 12/2003 | Court et al. | 435/455 |
| 2004/0092016 | A1 | 5/2004 | Court et al. | 435/455 |

FOREIGN PATENT DOCUMENTS

| | | |
|---|---|---|
| WO | WO 98/56943 | 12/1998 |
| WO | WO 00/05355 | 2/2000 |
| WO | WO 00/26396 | 5/2000 |
| WO | WO 00/36088 | 6/2000 |
| WO | WO 02/083889 A2 | 10/2002 |

OTHER PUBLICATIONS

Aslanidis, Charalampos, de Jong, Pieter J. and Schmitz, Gerd (1994). "Minimal Length Requirements of the Single-stranded Tails for Ligation-independent Cloning (LIC) of PCR Products," *Cold Spring Harbor Laboratory Press ISSN* 4, 172-177.
Aslanidis, Charalampos and de Jong, Pieter J. (1990). "Ligation-independent cloning of PCR products (LIC-PCR)," *Nucleic Acids Research*. 18, 6069-6074.
Baubonis, Wendy and Sauer, Brian (1993). "Genomic Targeting with Purified Cre Recombinase," *Nucleic Acids Research*. 21, 2025-2029.
Bouthier, Claire, Portemer, Christiane, Huber, Robert, Forterre, Patrick and Duget, Michel (1991). "Reverse Gyrase in Thermophilic Eubacteria," *Journal of Bacteriology*. 173, 3921-3923.
Cheng, C. et al., (2000), "DNA Strand Transfer Catalyzed by Vaccinia Topoisomerase: Ligation of DNAs Containing a 3' Mononucleotide Overhang," *Nucleic Acids Research*, 28(9): 1893-1898.
Cue, David and Feiss, Michael (1993). "The Role of *cos*B, The Binding Site for Terminase, The DNA Packaging Enzyme of Bacteriophase λ, in the Nicking Reaction," *Journal of Molecular Biology*. 234, 594-609.
Cue, David and Feiss, Michael (1993). "A Site Required for Termination of Packaging of the Phage λ Chromosome," *Proceedings Of The National Academy of Sciences*. 90, 9290-9294.
Fukata, Hideki, Mochida, Akemi, Maruyama, Naomi and Fukasawa, Hirosuke (1991). "Chloroplast DNA Topoisomerase I from Cauliflower," *Journal of Biochemistry*. 109, 127-131.
Fukuhara, Hiroshi (1995). "Linear DNA plasmids of yeasts," *Elsevier*. 131, 1-9.
Fukushige, Shinichi and Sauer, Brian (1992). "Genomic Targeting with a Positive-Selection *Lox* Integration Vector Allows Highly Reproducible Gene Expression in Mammalian Cells," *Proceedings Of The National Academy of Sciences*. 89, 7905-7909.
Hanai, Ryo, Caron, Paul R. and Wang, James C. (1996). "Human TOP3: A Single-Copy Gene Encoding DNA Topoisomerase III," *Proceedings Of The National Academy of Sciences*. 93, 3653-3657.
Heyman, John A., et al. (1999). "Genome-Scale Cloning and Expression of Individual Open Reading Frames Using Topoisomerase I-Mediated Ligation," *Genome Research*. 9, 383-392.
Higgins, R. Rachel and Becker, Andrew (1994). "Chromosome End Formation in Phage λ, Catalyzed by Terminase, is Controlled by Two DNA Elements of *cos, cos*N and R3 and by ATP," *Embo Journal*. 13, 6152-6161.
Higgins, R. Rachel and Becker, Andrew (1995). "Interaction of Terminase, the DNA Packaging Enzyme of Phage λ, with its *cos* DNA Substrate," *Journal of Molecular Biology*. 252, 31-46.
Hinnebusch, Joe and Tilly, Kit (1993). "Linear Plasmids and Chromosomes in Bacteria," *Molecular Microbiology*. 10, 917-922.
Keck, James L. and Berger, James M. (1999). "Enzymes That Push DNA Around," *Nature Structure Biology*. 6, 900-902.
Kim, Raymond A. and Wang, James C. (1992). "Identification of the Yeast TOP3 Gene Product as a Single Strand-specific DNA Topoisomerase," *Journal of Biology Chemistry*. 267, 17178-17185.
Meinhardt F., Schaffrath R. and Larsen, M. (1997). "Microbial Linear Plasmids," *Appl. Microbiol. Biotechnol*. 47, 329-336.

(Continued)

*Primary Examiner*—James S Ketter

(57) ABSTRACT

The invention provides cells and methods of circularizing linear DNA molecules. The cell is an isolated *Escherichia coli* cell which transiently expresses the Cre recombinase protein from an integrated Cre recombinase gene, and which is at least transiently repressed for RecBCD activity. The cells are used in a method of circularizing a linear DNA molecule comprising at least two loxP sites. The DNA molecule is introduced into the cells, and the linear DNA molecule is joined at said loxp sites.

18 Claims, 19 Drawing Sheets

OTHER PUBLICATIONS

Mondragon, Alfonson and DiGate, Russell (1999). "The Structure of *Escherichia coli*DNA Topoisomerase III," *Structure*. 7, 1373-1383.

Mukherjee, Sunil, Reddy, Malireddy K., Kumar, Dhirendra, and Tewari, Krishna K. (1994). "Purification and Characterization of a Eukaryotic Type 1 Topoisomerase from Pea Chloroplast," *Journal of Biological Chemistry*. 269, 3739-01.

Nadal, Marc, Couderc, Elisabeth, Duget, Michel and Jaxel, Christine (1994). "Purification and Characterization of Reverse Gyrase from Sulfolobus Shibatae," *Journal of Biological Chemistry*. 269, 5255-63.

Pan et al. "Ligation of Synthetic Activated DNA Substrates by Site-Specific Recombinatses and Topoisomerase I," *Journal of Biological Chemistry*. 1993. vol. 268, No. 5, pp. 3683-3689.

Rybchin, Valentin and Svarchevsky, Alexander N. (1999). "The plasmid prophase N15: A linear DNA with Covalently Closed Ends," *Molecular Microbiology*. 33, 895-903.

Sauer, Brian (1993). "Manipulation of Transgenes by Site-Specific Recombination: Use of Cre Recombinase," *Academic Press, Inc.* 225, 890-901.

Sauer, B. and Henderson, N., (2001). "The Cyclization of Linear DNA in *Escherichia coli* by Site-Specific Recombination," *Gene*. vol. 70, 331-341.

Shuman, Stewart and Moss, Bernard (1987). "Identification of a Vaccinia Virus Gene Encoding a Type I DNA Topoisomerase," *Proceedings Of The National Academy of Sciences*. 84, 7478-7482.

Slesarevi, Alexei I., et al. (1991). "DNA Topoisomerase III from Extremely Thermophilic Archaebacteria," *Journal of Biological Chemistry*. 19, 12321-12328.

Sternberg N., et al. (1986). "Bacteriophage P1 *Cre* Gene and its Regulatory Region. Evidence for Multiple Promoters and for Regulation by DNA Methylation," *J. Mol. Biol.*, vol. 187(2), 197-212.

International Search Report of International Application No. PCT/US01/05657.

European Search Report of European Application No. 01918206.2.

* cited by examiner

PCR product with Gam upstream of Cre

US 7,517,688 B2

METHOD FOR LIGATING NUCLEIC ACIDS AND MOLECULAR CLONING

RELATED APPLICATION

This application is a continuation-in-part of U.S. patent application Ser. No. 10/057,050, filed Jan. 25, 2002, which is a continuation of U.S. patent application Ser. No. 09/513,710, filed Feb. 25, 2000. The entire teachings of these disclosures are incorporated herein by reference.

TECHNICAL FIELD

The invention relates to methods, cells and kits useful for circularizing linear DNA molecules.

BACKGROUND OF THE INVENTION

Circularization of linear nucleic acid molecules often requires enzymatic steps. One alternative to circularizing linear DNA molecules is by site-specific recombination. A number of approaches for the joining of DNA molecules have been described using the Cre-loxP site-specific recombination system, including Sauer and Henderson, (1988), Gene 70, 331-341; WO 00/26396; WO 02/083889; and U.S. Pat. App. No. 2004/0092016.

SUMMARY OF THE INVENTION

It is an object of the invention to provide methods, compositions and microorganisms useful in the circularization of linear DNA molecules. This and other objects of the invention are provided by one or more of the embodiments described below.

In one aspect, microorganisms for biotechnology applications are provided. The microorganism is an isolated *Escherichia coli* cell which transiently expresses the Cre recombinase protein from an integrated Cre recombinase gene, and which is at least transiently repressed for RecBCD activity.

In another aspect, the present invention provides for a method of circularizing a linear DNA molecule comprising at least two loxP sites. The method comprises introducing the linear DNA molecule into an isolated *Escherichia coli* cell which transiently expresses the Cre recombinase protein from an integrated Cre recombinase gene, and which is at least transiently repressed for RecBCD activity. The linear DNA molecule is joined at the loxP sites.

In yet another aspect, the present invention provides for a kit for the circularization of a linear DNA molecule, comprising the cells described herein, and optionally an instruction manual and packaging material.

DETAILED DESCRIPTION OF THE INVENTION

Definitions

Figure 1:
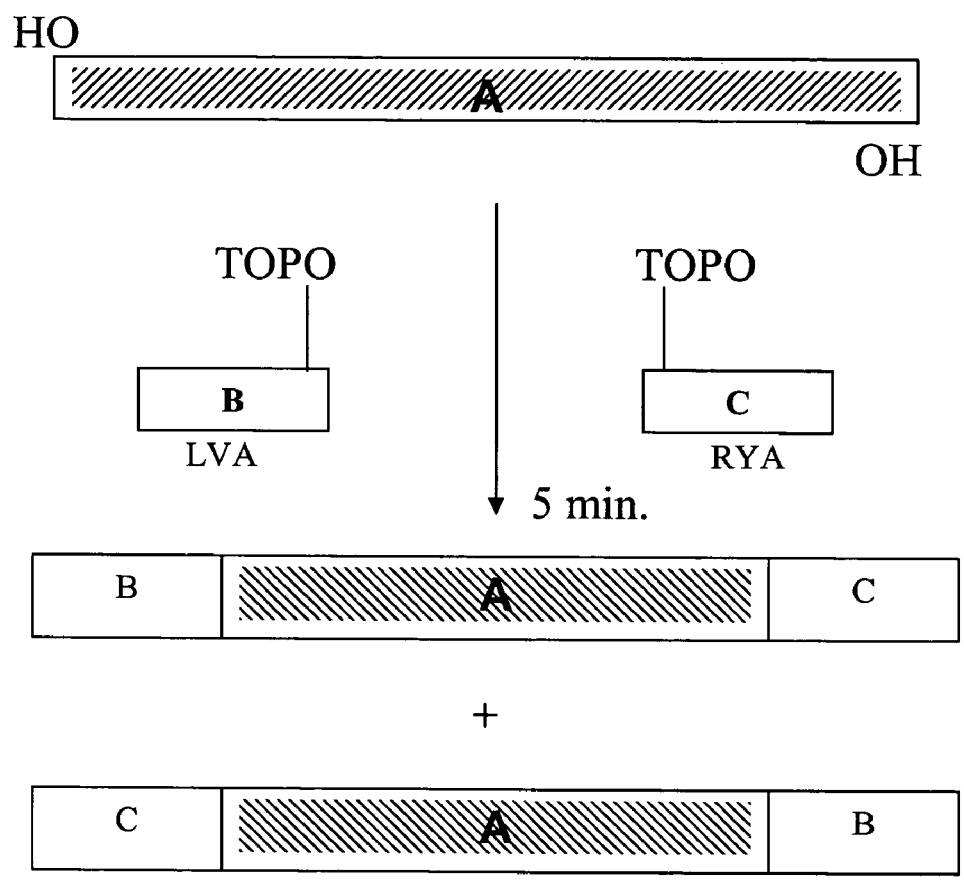
FIG. 1 shows the non-directional covalent joining of an insert molecule with 5'—OH groups on each end to a right vector arm and a left vector arm each comprising a topoisomerase polypeptide on one end only.

As used herein, the term "join" or "joining" refers to both covalent and noncovalent attachment of one nucleic acid to another, or one end of a nucleic acid to another end of a nucleic acid. "Covalent" joining refers to the attachment of one end of a nucleic acid strand to another end of a nucleic acid strand via a phosphate bond or to attachment of one end of a double-stranded nucleic acid to another double-stranded end via phosphate bonding on one or both strands. "Non-covalent" joining refers to attachment of one end of a nucleic acid to another end via annealing of a single-stranded region to each other; that is, no phosphate bond is generated in this embodiment.

"Ligate" or "ligated" refers to the covalent joining of two ends of one or more nucleic acid molecules.

"Complementary annealing" refers to annealing, or the pairing of bases, of complementary regions of one or more nucleic acids, and thus to the formation of hydrogen bonds and other non-covalent interactions between pairs of bases.

A "topoisomerase" is a polypeptide that is capable of covalently joining to at least one strand of a nucleic acid molecule and ligating that strand to another strand, as described hereinbelow. Topoisomerase according to the invention comprises type I topoisomerases.

"Bound to" refers to a covalent bonding of a topoisomerase polypeptide to a nucleic acid molecule.

"Nucleic acid molecule" refers to a double-stranded nucleic acid, unless otherwise specified.

"One end only" refers to the presence of a topoisomerase polypeptide at one end of a nucleic acid molecule, where the nucleic acid molecule contains two ends.

The term "site" is meant to designate a contiguous stretch of nucleotides, e.g., 1-100 bases in length, usually 5-25 bases in length, e.g., 8-16 bases, that is susceptible to (i.e., a substrate for) modification by an enzyme that modifies nucleic acids, e.g., a ligase or a restriction enzyme.

A "cloning substrate site", as used herein, is a site occurring on a nucleic acid molecule for the covalent or non-covalent joining of nucleic acid sequences or for recombination. Examples of cloning substrate sites include cos sites, LIC sites, sites for site-specific recombination, such as lambda attachment elements or loxP sites, sites for homologous recombination, and ligation substrate sites.

A "ligation substrate site", as used herein, is a site occurring on a nucleic acid molecule of the invention that is capable of becoming covalently joined to another nucleic acid molecule in the presence of a ligase enzyme, such as DNA ligase.

A "vector arm" or a "linear arm", as used herein, is a linear nucleic acid molecule, and is preferably a portion or fragment of a bacteriophage or plasmid genome.

"Directional" cloning refers to a cloning method in which, by selecting steps in the method, one can obtain a desired orientation of a given nucleic acid molecule upon cloning into another nucleic acid molecule or between two other nucleic acid molecules; as used herein, "orientation" may refer to 5' to 3' with reference to a given open reading frame or a given control region or a known sequence. Thus, for example, an insert molecule may contain an open reading frame having a 5'-3' orientation with respect to transcription and the insert molecule may be directionally cloned between a left and right vector arms such that the ligated (cloned) molecule comprises, from 5' to 3': left vector arm, 5' insert 3', right vector arm. "Non-directional" cloning refers to cloning methods which produce a ligated molecule in which the insert, for example, appears between the two arms in either orientation.

As used herein, a genetic construct which is "integrated" refers to a construct which has been inserted into the genome of the bacterium (i.e., into the bacterial chromosome).

As used herein, an "inducible" expression system refers to any expression system in which the transcription level can be modulated by at least 2 fold (for example, at least 3 fold, 5 fold, 10 fold, 15 fold, 20 fold, 30 fold, 100 fold or more). As used herein, an "inducible" expression system encompasses expression systems which can be induced, for example, by an inducer chemical (e.g., arabinose, lactose, IPTG, etc), a stimulus (e.g., heat, cold, etc.), or growth conditions (e.g., cell density, medium pH, etc). An "inducible" expression system also encompasses any expression system which can be down-regulated, for example, expression systems which can be down-regulated upon addition of a chemical (e.g., glucose-repressible), environmental stimulus, and the like.

As used herein, a cell is said to "transiently express" the Cre recombinase protein when the presence of Cre is transient, or when the abundance of Cre varies depending on the applied condition. Ideally, the Cre recombinase protein is present in the cell at the moment that the linear DNA molecule is introduced, and substantially reduced (i.e., at least 2-fold reduced, for example, 3 fold, 5 fold, 10 fold, 20 fold, 100 fold reduced or more) in abundance or absent during subsequent plasmid purification, for example as measured using methods described in Kaczmarczyk & Green (2003) Nucl. Acid Res. 31, e86. As used herein, a cell that "transiently expresses" the Cre recombinase also contemplates a cell in which the expression is never totally abolished. Therefore, even if the protein is present at all times, a cell is said to "transiently express" Cre if the expression levels can be manipulated (e.g., by addition of an inducer) such that its abundance is significantly higher (e.g., at least 2-fold higher, for example, 3 fold, 5 fold, 10 fold, 20 fold, 100 fold higher or more) at one point (e.g., at the point that the linear DNA molecule is introduced) than at another (e.g., when cells are collected for plasmid purification). One can "transiently express" the Cre recombinase that is expressed at a low, basal level, for example, by addition of an inducer. Alternatively, a repressor can be removed to achieve transient expression.

As used herein, a cell is "transiently repressed" for RecBCD activity when the ATP-dependent nuclease activity of the RecBCD enzyme is substantially reduced (i.e., at least 50% up to 100% reduced, for example 60%, 70%, 75%, 80%, 90%, 95%, 99% up to 100%) during the time that the linear DNA molecule is introduced to the cell, when compared with a wild-type cell, and as measured, for example, as described in Boehmer & Emmerson, (1991) Gene 102, 1. For example, the detectable ATP-dependent nuclease activity of the RecBCD enzyme can be repressed transiently by, for example by replacing its promoter with one that can be repressed by selected stimuli, whether environmental, chemical or otherwise, and adding the repressor to the growth medium to repress its expression. In addition, a cell that transiently expresses an inhibitor of the ATP-dependent nuclease activity of the RecBCD enzyme is also said to be "transiently repressed" for RecBCD activity. ATP-dependent nuclease activity of RecBCD can be measured in vitro as described in the art (e.g., Boehmer & Emmerson, (1991) Gene 102, 1). As used herein, a cell that is "at least transiently repressed" for RecBCD activity encompasses both a cell that is "transiently repressed" for RecBCD activity, as well a cell that has continuously reduced or abolished RecBCD activity when compared with a wild-type cell, for example, as a result of a mutation within the recB, recC or recD gene.

Insert Polynucleotide Molecules

Insert polynucleotide molecules comprise isolated and purified double-stranded DNA, double-stranded RNA, or double-stranded DNA/RNA hybrid nucleic acids. An insert molecule can be a full-length molecule or a fragment of a full-length molecule. Further, an insert molecule can be naturally-occurring, i.e., found in nature or recombinant.

Preferably, insert polynucleotides are isolated free of other components, such as proteins and lipids. Insert polynucleotides can be made by a cell and isolated or can be synthesized in the laboratory, for example, using an automatic synthesizer or an amplification method such as PCR. Where an insert polynucleotide is prepared by PCR, the insert is generated using a pair of primers comprising a 3'-primer and a 5'-primer. Both the 3'-primer and the 5'-primer can comprise a 5'-hydroxyl group to produce an insert with 5'-hydroxyl groups (5'—OH) on both ends. Alternatively, one of the primers can comprise a 5'-hydroxyl group and one can comprise a 5'-phosphate group to produce an insert with a 5'—OH group on one end and a 5'-phosphate (5'-P) group on the other end. Optionally, both the 3'-primer and the 5'-primer can comprise a 5'-phosphate group to produce an insert with 5'-P groups on both ends.

Molecules Flanking an Insert Molecule

An insert polynucleotide molecule can be covalently joined to several types of molecules, such as a double-stranded DNA, a double-stranded RNA, and a double-stranded DNA/RNA hybrid molecule. Preferably, an insert polynucleotide molecule is covalently joined to a vector molecule or to vector molecules such as a linear arm of a plasmid or bacteriophage. Vectors suitable for ligation of an insert molecule include bacteriophage, such as bacteriophage lambda, including, but not limited to lambda insertion vectors such as Lambda ZAP®II vector, ZAP Express® vector, Lambda ZAP®-CMV vector (Stratagene), lambda gt10, and lambda gt11. Lambda replacement vectors, for example Lambda FIX®II vector, Lambda DASH®II vector, and Lambda EMBL3 and Lambda EMBL4 (Stratagene) can also be used as vectors.

Both prokaryotic and eukaryotic linear plasmids can be used as vectors. See e.g., Meinhardt et al. (1997) Appl. Microbiol. Biotechnol. 47:329-36; Fukuhara, (1995) FEMS Microbiol. Lett.131:1-9; Hinnebusch & Tilly, (1993) Mol Microbiol. 10:917-22. For example, the plasmid prophage N15 of E. coli is a suitable linear plasmid vector. See Rybchin & Svarchevsky (1999) Mol. Microbiol. 33:895-903.

Vector nucleic acid polynucleotides, such as bacteriophage and plasmids can be isolated and purified from cells carrying these elements according to methods well known in the art. See e.g. MOLECULAR CLONING: A LABORATORY MANUAL (Sambrook et al., eds., Cold Spring Harbor Laboratory Press, Cold Spring Harbor, 1989) and Ausubel (CURRENT PROTOCOLS IN MOLECULAR BIOLOGY (Ausubel et al., eds., John Wiley & Sons, New York, 1987)). Additionally, many bacteriophage and plasmid vectors are commercially available. The bacteriophage or plasmid nucleic acid can be prepared, if necessary by cleavage with an appropriate restriction enzyme such that the digested bacteriophage or plasmid nucleic acid is compatible with an insert molecule.

Preferably, an insert molecule is covalently joined to right and left lambda linear vector arms such that the insert molecule is positioned between right and left lambda linear vector arms. In lambda insertion vectors, a left vector arm can comprise lambda nucleic acids occurring to the left of the insertion site and a right vector arm can comprises lambda nucleic acids occurring to the right of the insertion. In lambda replacement vectors, a left lambda arm comprises lambda nucleic acid occurring to the left of the nucleic acids to be replaced by the insert nucleic acids and a right lambda arm comprises lambda nucleic acids occurring to the right of the nucleic acids to replaced by the insert nucleic acids. Lambda vectors can vary in nucleic acid sequence; however, the left arm can typically comprise the head and tail genes A-J, while the right arm can typically comprise from PR through a cosR site of a lambda genome.

Preferably, the vector or flanking molecule to which the insert is to be covalently joined is a linear molecule comprising a topoisomerase covalently linked to only one end of the linear molecule. A double-stranded DNA, double-stranded RNA, or double-stranded DNA/RNA molecule with one topoisomerase molecule bound to one end of the DNA or RNA molecule is a univalent molecule. DNA topoisomerases catalyze a conversion in the linking number of a double-stranded DNA molecule. The linking number is the number of times one DNA strand crosses over the second DNA strand in space. Type 1 topoisomerases act by making a transient break in one strand of a nucleic acid. A type 1 topoisomerase first binds to a nucleic acid and nicks one strand of the nucleic acid. A stable complex is formed where the free 3'-phosphate end of the nicked strand is covalently bound to a tyrosine residue of the enzyme. The second strand is pulled through the gap in the first strand and the gap is then sealed by the enzyme. The gap can be sealed at the same bond originally nicked or the complex can combine with a heterologous nucleic acid, such as an insert molecule, that has a 5'-hydroxy end. Where the complex is combined with a heterologous nucleic acid, a recombinant molecule is formed.

Type 1 topoisomerases include, but are not limited to E. coli topoisomerase I (Keck et al., (1999) Nat. Strut. Biol. 6:900), E. coli topoisomerase III (Mondragon et al., (1999) Structure Fold. Des. 7:1373), S. cerevisiae topoisomerase III (Kim et al., (1992) J. Biol. Chem. 267:17178), human topoisomerase III (Hanai et al., (1996) Proc. Natl. Acad. Sci. 93:3653), the type I topoisomerase from chloroplasts (Mukherjee et al. (1994) 269:3793; Fukata et al. (1991) J. Biochem (Tokyo) 109:127), thermophilic reverse gyrases (Nadal et al., (1994) J. Biol. Chem. 269:5255; Slesarev et al., (1991) J. Biol. Chem. 266:12321; Bouthier de la Tour et al., (1991) J. Bact. 173:3921), thermophilic D. amylolyticus topoisomerase III (Slesarev et al., (1991) J. Biol. Chem. 266:

12321), and vaccinia DNA topoisomerase I (Shuman et al., (1987) Proc. Natl. Acad. Sci. 84:7478). Site-specific type I DNA topoisomerases are particularly useful in the invention. Site-specific type I DNA topoisomerases include vaccinia topoisomerase and pox virus topoisomerases.

A topoisomerase enzyme can be covalently linked to a vector or flanking molecule by, for example, the method of Heyman et al. (Genome Res. (1999) 9:383). Briefly, Vaccinia DNA topoisomerase cleaves the phosphodiester backbone of one strand of a nucleic acid at a consensus pentopyrimidine element: 5'-C/TCCTT-3' (SEQ ID NO:1). This element can be added onto the end of a vector or flanking molecule. Vaccinia topoisomerase can then be incubated with the vector or flanking molecule such that the topoisomerase becomes covalently bound to the underlined T in the C/TCCTT sequence. Optionally, nuclease treatment, such as exonuclease III treatment can be used to remove single strand ends from the element such that a blunt-ended insert fragment with topoisomerase bound to the molecule is formed.

Optionally, the molecule to which the insert is to be covalently joined is a linear molecule comprising a ligation substrate site at a first end of the linear molecule. A ligation substrate site comprises a site for nucleic acid ligation that is mediated by a ligase enzyme. A ligation substrate site can comprise any double-stranded nucleic acid that has blunt ends or protruding termini that can be covalently joined to another nucleic acid molecule in the presence of a ligase enzyme. Preferably, the ligation substrate site comprises a 5'-phosphate group and is complementary to one end of an insert molecule. A ligation substrate site can be produced by, for example cleaving a double-stranded nucleic acid molecule with a restriction enzyme that produces blunt-ended termini, 5'- protruding ends, or 3'-protruding ends and purifying the nucleic acid molecule. A ligation between a linear molecule comprising a ligation substrate site and an insert molecule takes place in the presence of a ligase enzyme such as bacteriophage T4 DNA ligase or Pfu DNA ligase (Stratagene). Preferably, the vector or flanking molecule to which the insert is to be covalently joined is a linear molecule comprising a topoisomerase covalently linked to only one end of the molecule or a ligation substrate site at one end of the linear molecule. The second end of the linear molecule preferably comprises a cloning substrate site such as, a cos site, a LIC site, a site-specific recombination site (such as a loxP site or lambda attachment element), a homologous recombination site or a ligation substrate site.

A bacteriophage lambda genome has cos sites at the ends of the genome. See, LAMBDA II (Roger W. Hendrix, ed., Cold Spring Harbor Laboratory Press) 1983; Higgins et al., (1995) J. Mol. Biol. 252:31; Higgins et al., (1994) EMBO J. 13:6152; Cue et al., (1993) J. Mol. Biol. 234:594; Cue et al., (1993) Proc. Natl. Acad. Sci. USA 90:9290. Cleavage occurs at a left cos site (as defined on a standard lambda map) to generate a free end that is inserted into a capsid. The insertion of nucleic acid continues until a right cos site is encountered. Cleavage occurs at the right cos site to generate the second end. Any nucleic acid molecule that is contained between two cos sites can be packaged. A nucleic acid molecule comprising a cos site, a fragment of a cos site, a mutant of a cos site, or a variant of a cos site can be isolated from a preparation of bacteriophage lambda DNA or may synthesized in the laboratory. A nucleic molecule comprising a cos site can be ligated to the end of the molecule to which the insert is to be covalently joined. Alternatively, a cos site can be added to the end of a molecule to which the insert is to be covalently joined using standard molecular biology cloning techniques such as PCR.

In the methods of the invention distal ends (i.e., the ends of vector arms not covalently joined to an insert molecule) of vector arms containing terminal cos sites can be readily annealed to one another in E. coli host cells by virtue of their explicit sequence. cos sites do not appreciably anneal in vitro at room temperature.

A ligation-independent cloning (LIC) site can be any size, but is preferably 12 to 13 nucleotides or longer. Sites longer than 12-13 nucleotides may work more efficiently, e.g., up to 24 bases, or up to 48 bases or longer. See Aslanidis and de Jong, (1990) Nucleic Acids Res. 18:6069. The 12-13 nucleotide terminus can comprise any nucleic acid sequence; however, preferably one or none of the nucleotides of a 3' strand of the 12-13 nucleotide terminus is an adenosine. A nucleic molecule comprising a LIC site can be ligated to the ends of the vector or flanking molecule to which the insert is to be covalently joined. Alternatively, a LIC site can be added to the end of a vector or flanking molecule to which the insert is to be covalently joined using standard molecular biology cloning techniques, such as by PCR.

Where the second end of a linear molecule comprises a LIC site, a ligated insert/vector molecule will be formed that comprises LIC ends at each end of the ligated insert/vector molecule. The insert can then be joined to a LIC ready vector. Aslanidis et al., (1994) PCR Methods Appl. 4:172; Aslanidis and de Jong (1990) Nucleic Acids Res. 18:6069. Briefly, the ligated insert/vector molecule is subjected to treatment with, for example, Pfu DNA polymerase in the presence of dATP. In the absence of dTTP, dGTP, and dCTP, the 3'- to 5'- exonuclease activity of Pfu DNA polymerase removes 12 to 13 nucleic acids from the 3'-ends of the ligated insert/vector molecule. This activity continues until the first adenine is encountered. This produces a ligated insert/vector molecule with 5'-extended single-stranded tails that are complementary to the single-stranded tails of a LIC ready vector. The ligated insert/vector molecule will anneal to the LIC ready vector without further enzymatic treatment.

The second end of the linear molecule can further comprise a site for homologous recombination or a site for site-specific recombination. Homologous recombination is a recombination event occurring between homologous sequences of nucleic acids. The enzymes responsible for homologous recombination can use any pair of homologous sequences as substrates, although some types of nucleic acid sequences can be favored over others. Sites for homologous recombination comprise nucleic acid sequences that are homologous to the nucleic acid sequences of a cloning vector, such as a circular plasmid. The sites can insert (or integrate) into a cloning vector by homologous recombination, thereby inserting or displacing a nucleic acid sequence, or deleting a nucleic acid sequence altogether.

To create a homologous recombinant plasmid cloning vector, a plasmid cloning vector is prepared which contains homologous recombination nucleic acid sites that are substantially homologous to those sites occurring on the ligated insert/vector of interest. Substantially homologous nucleic acid sequences are those nucleic acid sequences that share sufficient nucleic acid sequence homology to provide for sufficient homologous recombination between a ligated insert/vector sequence and a plasmid cloning vector. Sufficient nucleic acid sequence homology is the amount which provides for homologous recombination at a frequency which allows for detection of plasmid cloning vectors in which homologous recombination and integration of the ligated vector/insert has occurred. Substantially homologous nucleic acid sequences preferably share regions with about 60% to 100% nucleic acid sequence homology, and more preferably about 75% to 100% homology in the nucleic acid sequence. A site for homologous recombination can be present in the plasmid cloning vector in two or more copies. The homologous recombination sites in the plasmid cloning vector are of sufficient length for successful homologous recombination with a ligated insert/vector molecule. Typically, each homologous recombination site is at least 30, 75, 100, 150, 250, 500, or 1000 base pairs. The ligated insert/vector sequence comprises these substantially homologous recombination sites at both the 5'- and 3-' ends. The ligated insert/vector sequence is transformed into a host cell, such as an *E. coli* cell that contains the plasmid cloning vector. Preferably, the host cell is RecA+. RecA is the product of the recA locus of *E. coli* and is a protein that is involved in recombination.

In addition to homologous recombination as described above, enzyme-assisted site-specific integration systems are known in the art and can be applied to integrate a ligated nucleic acid insert/vector molecule at a predetermined location in a cloning vector molecule. Site-specific recombination is a recombination event between specific pairs or sequences. The recombination event involves specific sequences of nucleic acids comprising a short stretch of homology necessary for the recombination event. The enzymes involved in the recombination event will act only on this particular pair of target sequences. Examples of such enzyme-assisted integration systems include the Cre recombinase/loxP target system (e.g., as described in Baubonis and Sauer (1993) Nucl. Acids Res. 21:2025; and Fukushige and Sauer, (1992) Proc. Natl. Acad. Sci. USA 89:7905). A loxP site (locus of crossing over) comprises two 13 base pair inverted repeats separated by an 8 base pair asymmetric spacer region:

```
ATAACTTCGTATA ATGTATGC  TATACGAAGTTAT (SEQ ID NO:2)
Inverted      Spacer    Inverted
repeat                  repeat
```

A loxP site of the invention comprises variants and mutants of this sequence that function to produce site-specific recombination. Cre is a 38 kDa recombinase protein from bacteriophage P1 which mediates intramolecular and intermolecular site-specific recombination between loxP sites. Sauer, (1993) Methods Enzymol. 225:890. A loxP site is an asymmetrical nucleotide sequence and two lox sites on the same DNA molecule can have the same or opposite orientation with respect to one another. See U.S. Pat. No. 4,959,317. Where two loxP sites occur in the same orientation on a nucleic acid molecule, recombination between the loxP sites results in the deletion of the nucleic acid segment located between the two loxP sites and a connection between the resulting ends of the original nucleic acid molecule. The deleted nucleic acid molecule will form a circular molecule of nucleic acid. The original nucleic acid molecule and the circular nucleic acid molecule will each contain a single loxP site. Where two loxP sites occur in opposite orientations on the same nucleic acid molecule recombination will result in an inversion of the nucleotide sequence of the nucleic acid segment located between the two loxP sites. Further, where two loxP sites occur on each of two nucleic acid segments, reciprocal exchange of nucleic acid segments proximate to the loxP sites can occur.

Methods of Covalently Joining

Insert polynucleotide molecules comprising a 5'—OH group on each end or a 5'—OH on one end and a 5'-phosphate group on the other end can be covalently joined to flanking polynucleotide molecules such that non-directional or directional covalent joining is achieved. Where an insert polynucleotide molecule has a 5'—OH group on each end non-directional covalent joining of the insert to flanking polynucleotide molecules results. For example, where an insert polynucleotide (I) with a 5'—OH group at each end is covalently joined to flanking molecules, for example, a left vector arm (LVA) and a right vector arm (RVA) each with a topoisomerase polypeptide covalently joined at only one end, the result will be non-directional covalent joining of the molecules. A LVA, RVA, and insert molecule are incubated together under conditions sufficient to permit their topoisomerase-mediated covalent joining to form a covalently joined nucleic acid molecule where the insert molecule is positioned between the LVA and RVA. Four different covalently joined products (ligated insert/vector molecules) will result: LVA-I-LVA, RVA-I-RVA, LVA-I-RVA, and RVA-I-LVA. Only the LVA-I-RVA and RVA-I-LVA products are viable replication competent entities. Where an insert polynucleotide has a 5'—OH group on one end and a 5'-phosphate group on the other end directional covalent joining of the insert to flanking polynucleotide molecules can result. For example, where an insert polynucleotide is covalently joined to a flanking molecules such as a LVA and a RVA, each comprising a topoisomerase covalently bound to only one end, directional covalent joining of the molecules can result. A first vector arm, for example, a LVA is covalently joined to an insert molecule at the 5'—OH end by incubating a LVA and an insert molecule together under conditions sufficient to permit topoisomerase-mediated covalent joining to form a ligated nucleic acid molecule where the insert molecule is positioned adjacent to a LVA to create LVA-I-phosphate. The 5'-phosphate end of the insert is unable to be ligated to the LVA or RVA because either the LVA or RVA has a 3'-phosphate, which is the site to which a topoisomerase polypeptide is joined to the LVA and RVA. The LVA-I-5'-phosphate is treated with phosphatase, under conditions which permit removal of a 5'-phosphate group from the ligated nucleic acid resulting in a LVA-I-5'—OH molecule. The LVA-I-5'—OH molecule is then covalently joined to the RVA to form LVA-I-RVA by incubating a LVA-I-5'—OH molecule with a RVA under conditions which permit topoisomerase covalent joining to form a ligated molecule where the insert molecule is positioned between a RVA and a LVA (a ligated insert/vector molecule).

Alternatively, an insert polynucleotide comprising a 5'—OH group on one end and a 5'-phosphate group on the other end can be covalently joined in a directional manner to a flanking nucleic acid molecule comprising a topoisomerase polynucleotide on only one end and to a second flanking molecule comprising a ligation substrate site on one end. For example, an insert molecule can be covalently joined to a flanking nucleic acid molecule, such as a LVA, comprising a topoisomerase polypeptide on only one end and to, for example, a RVA comprising a ligation substrate end on one end. The insert LVA, and RVA are covalently joined by topoisomerase-mediated joining and ligase-mediated joining under conditions sufficient to form a ligated nucleic acid where the insert molecule is positioned between a LVA and a RVA to form LVA-I-RVA (a ligated insert/vector molecule). This reaction can take place in one step.

After the ligated insert/vector molecule described above has been constructed, the two vector arms can be non-covalently or covalently joined to one another, at the ends distal to the covalently attached topoisomerase polypeptide or ligation substrate site (i.e., at their free ends), by a number of methods such that a circular molecule is formed. For example, the ends of the ligated insert/vector molecule can comprise ligase substrate sites or complementary nucleic acid sequences such that the ends can be joined by ligase enzyme mediated ligation or complementary sequence annealing. Further, where the ends of the ligated insert/vector molecule comprise 5'—OH groups the ends can be joined by topoisomerase mediated ligation using a polynucleotide comprising a topoisomerase polypeptide at both ends of the polynucleotides. See e.g. U.S. Pat. No. 5,766,891. Further, where the ends of the ligated insert/vector molecule comprise in vitro or in vivo site-specific recombination sites or in vivo homologous recombination sites the ligated insert/vector molecule can be recombined into a circular plasmid containing the same recombination sites.

The methods of directional and non-directional covalently joining of nucleic acid molecules are useful in, for example, end-labeling, ligand tagging, and molecular cloning.

Methods of Molecular Cloning Insert polynucleotide molecules comprising a 5'—OH group on each end or a 5'—OH on one end and a 5'-phosphate group on the other end can be cloned into vector molecules such that non-directional or directional cloning is achieved.

Non-directional cloning can be accomplished by cloning a polynucleotide insert molecule comprising 5'—OH groups at both ends of the molecule into a nucleic acid vector. For example, an insert polynucleotide (I) with a 5'OH group at each end can be cloned into a vector, such as a left vector arm (LVA) and a right vector arm (RVA) where each vector arm has a topoisomerase polypeptide covalently joined at only one end of the vector arm. The result will be non-directional covalent joining of the molecules. Preferably, the LVA and RVA molecules have a cloning substrate site, such as a cos site, a LIC site, a loxP site, a site for homologous recombination, a site for site-specific recombination, or a ligase substrate site at the other end of the molecule. A LVA, RVA, and insert molecule are incubated together under conditions sufficient for topoisomerase-mediated covalent joining of the molecules to form a ligated nucleic acid wherein the insert molecule is positioned between the LVA and RVA. Four different covalently joined products will result: LVA-I-LVA, RVA-I-RVA, LVA-I-RVA, and RVA-I-LVA (ligated insert/vector molecules). Only the LVA-I-RVA and RVA-I-LVA products are viable replication competent entities.

Directional cloning can be accomplished by cloning a polynucleotide insert molecule comprising a 5'—OH group at one end of the molecule and a 5'-phosphate group at the other end into a nucleic acid vector. For example, an insert polynucleotide (I) with a 5'OH group at one end and a 5'-phosphate at the other end can be cloned into a linear cloning vector, where the linear cloning vector has a topoisomerase polypeptide covalently joined at one end and a ligation substrate site at the other end. The insert polynucleotide, the linear cloning vector, and a ligase are incubated together under conditions sufficient for their covalent joining to form a ligated circular vector (a ligated insert/vector molecule). The circular vector can then be transformed into a host cell.

Directional cloning can also be accomplished by cloning an insert polynucleotide having a 5'—OH group on one end and a 5'-phosphate group on the other end into a vector where the vector comprises, for example, two vector arm molecules comprising a topoisomerase polynucleotide at only one end and a cloning substrate site at the other end. For example, a first vector arm, LVA, is covalently joined to an insert molecule at the 5'—OH end by incubating a LVA and an insert molecule together under conditions sufficient to permit topoisomerase-mediated covalent joining to form a ligated nucleic acid molecule where the insert molecule is positioned adjacent to a LVA to create LVA-I-phosphate. The 5'-phosphate end of the insert is unable to be ligated to the LVA or RVA because a topoisomerase polypeptide is joined to the LVA and RVA at the 5'-phosphate. The LVA-I-5'-phosphate is treated with phosphatase, under conditions which permit removal of a 5'-phosphate group from the ligated nucleic acid resulting in a LVA-I-5'—OH molecule. The LVA-I-5'—OH molecule is then covalently joined to the RVA to form LVA-I-RVA by incubating a LVA-I-5'—OH molecule with a RVA under conditions which permit topoisomerase covalent joining to form a ligated molecule where the insert molecule is positioned between a RVA and a LVA (a ligated insert/vector molecule). Preferably, the cloning substrate site is a cos site, a LIC site, a loxP site, a site for homologous recombination, a site for site-specific recombination, or a ligation substrate site.

Alternatively, directional cloning can be accomplished with an insert polynucleotide comprising a 5'—OH group on one end and a 5'-phosphate group on the other end and two vector molecules. One vector molecule comprises a topoisomerase polynucleotide on only one end and a cloning substrate site on the other end. The other vector molecule comprises a ligation substrate site on one end and a cloning substrate site on the other end. An insert, a first vector molecule comprising a topoisomerase polypeptide at one end and a cloning substrate site at the other end, such as a LVA, and a second vector molecule such as a RVA comprising a ligation substrate site at one end and a cloning substrate at the other end are covalently joined by topoisomerase-mediated joining and ligase-mediated joining under conditions sufficient to form a ligated nucleic acid where the insert molecule is positioned between the LVA and the RVA vector molecules (a ligated insert/vector molecule). Preferably, the cloning substrate site is a cos site, a LIC site, a loxP site, a site for homologous recombination, a site for site-specific recombination, or a ligation substrate site.

Where the ligated insert/vector molecule comprises cos sites at each end, the linear molecule can be transformed directly into a host cell. Where the ligated insert/vector molecule comprises LIC ends at each end, the LIC ends can be annealed to a circular plasmid vector with LIC compatible ends. The circular molecule can be transformed into a host cell. Where the ligated insert/vector molecule comprises loxP sites on both ends, the ligated insert/vector molecule can be recombined into a circular plasmid in vitro in the presence of Cre recombinase. The recombinant circular plasmid can then be transformed into a host cell. Alternatively, a ligated insert/vector molecule with loxP sites at both ends of the molecule can be directly transformed into a host cell, such as E. coli harboring a plasmid suitable for site-specific recombination. The host cell may be recA+or recA-, and is preferably recA-. Where the covalently joined insert/vector molecule comprises sites for homologous recombination at each end, the covalently joined insert/vector molecule can be directly transformed into a suitable host cell harboring a plasmid suitable for homologous recombination.

The covalently joined insert/vector can be transformed into a prokaryotic or eukaryotic cell. Preferably, the covalently joined insert/vector is transformed into a prokaryotic host cell, such as a bacteria cell such as E. coli. Transformation of a ligated insert/vector molecule into a host cell can be done by any method known in the art. Methods for transformation of host cells can be found in Sambrook et al. and Ausubel and include, but are not limited to transfection, chemical transformation, electroporation, and lipofection. Where a bacteriophage lambda vector has been used according to the invention, the ligated insert/lambda vector can be packaged in vitro and then transfected into host cells, such as XLI-Blue E. coli. See e.g. Sambrook et al.

Host Cells

In another aspect, bacterial cells useful for circularization of linear DNA molecules are disclosed. The bacterial cell is an isolated bacterial cell, for example a gram negative bacterium, for example an isolated *Escherichia coli* cell, which transiently expresses the Cre recombinase protein and which is at least transiently repressed for RecBCD activity.

In one embodiment, the cell contains the coding sequence for the Cre recombinase protein operably linked to an inducible promoter. The Cre recombinase gene can be incorporated into the bacterial chromosome (i.e., integrated), provided on a plasmid, or both. In one embodiment, the cell transiently expresses the Cre recombinase protein from an integrated construct. The inducible promoter can be any known in the art, and include the galactose, lactose, tac, arabinose, rhamnose, tet, or trp promoters.

In one embodiment, the inducible promoter is the an arabinose-inducible promoter, for example the arabinose promoter of *E. coli*. Expression systems using the arabinose operon from *E. coli* has been well described (WO0173082 A2; Hirsh & Schleif, (1973) J Mol Biol 80(3), 433-44; Hahn, et al. (1984) J Mol. Biol 180(1), 61-72; Kosiba & Schleif, (1982) Mol. Biol 156(1), 53-66, each incorporated by reference). In another embodiment, the inducible promoter is a modified arabinose promoter, that is mutated to reduce basal levels of Cre protein expression. Modifications to reduce basal expression levels of Cre include introducing mutations into the araB promoter region, for example, the ribosome binding site, replacement of the start codon from ATG to GTG, and elimination by mutagenesis of cryptic start sites. Modifications of this type are described further in Example 10.

In addition to its role in recombination, the RecBCD enzyme is a nuclease that selectively hydrolyzes linear double-stranded DNA (dsDNA) to deoxynucleotides. The reaction is ATP-dependent, and does not affect closed circular supercoiled or nicked circular dsDNAs. For example, the RecBCD enzyme, which plays a critical role in recombination and repair of double-stranded DNA (dsDNA) breaks (Kowalczykowski et al. (1994) Microbiol Rev 58: 401-465), is also a major exonuclease activity (ExoV) which rapidly degrades linear DNA molecules, thereby inhibiting certain types of recombination (Telander-Muskavitch & Linn (1981) Enzymes 14A: 233-250). Reduction or elimination of RecBCD activity, in particular the ATP-dependent nuclease activity, which can result in reduced recombination efficiency, is therefore preferred. Therefore, in one embodiment, the cells useful for the circularization of linear DNA molecules are at least transiently repressed in RecBCD activity. Preferably, the cells are reduced in the ATP-dependent nuclease activity of the RecBCD enzyme at the time the linear DNA molecule is introduced into the cell. Therefore, in one embodiment, the cell contains one or more mutations within the recB gene, the recC gene, or both. In another embodiment, the RecBCD gene is driven by a repressible promoter. In still another embodiment, the cell is recBC⁻.

In yet another embodiment, the cell comprises an inducible construct which encodes an inhibitor of the RecBCD enzyme, in particular the ATP-dependent exonuclease activity of RecBCD. Examples of such inhibitors include the lambda Gam, the P22 Abc2, and T3-phage gene 5.9 product (See, for example, Poteete et al. (1988) J Bacteriol. 170:2012-21; Marsic et al. (1993) J Bacteriol. 175:4738-43; Murphy, (1991) J Bacteriol. 173: 5808-5821). Such inhibitors can be expressed at least transiently (i.e., either constitutively or transiently). It is only important that the inhibitor be present in the cell at the time the linear DNA is introduced into the cell, in order to minimize degradation of linear DNA at the time it is introduced into the cell. In one embodiment, the inhibitor of the RecBCD enzyme is the lambda Gam. In another embodiment, the inhibitor is the 5.9 gene product from phage T3. Gam is a protein encoded by the lambda genome involved in double strand break repair homologous recombination. Gam has been shown inhibit cellular nuclease activity such as that encoded by the RecBCD system of *E. coli*.

As previously noted, at the time the linear DNA molecule is introduced to the cell, it is preferable that the cell contains or expresses the Cre recombinase. Furthermore, reduction in the ATP-dependent exonuclease activity of the RecBCD enzyme is preferable. Therefore, in one embodiment, a host cell expresses both the Cre recombinase and an inhibitor of the RecBCD enzyme selected, for example, from the group consisting of lambda Gam, P22 Abc2, and T3-phage gene 5.9 product. According to this embodiment, the Cre recombinase and the inhibitor are expressed using an inducible promoter, for example in an integrated expression construct. In one embodiment, the inducible promoter is an arabinose-inducible promoter.

The cells described herein can be used for circularization of linear pieces of DNA. The cells can be used to circularize a single piece of DNA, containing two loxP sites. Alternatively, the cells can be used to circularize a plurality of linear DNA molecules, each containing at least two loxp sites. The only requirement is that at least two directly repeating loxP sites be present on each of the DNA molecules needing to be circularized.

In another embodiment, the cells are competent for transformation. Any of the well-established methods of generating competent cells that are known in the art can be used. One method involves growing cells to log phase or early stationary phase and exposing the cells to $CaCl_2$ at 0° C. (see, e.g., Sambrook, et al., *Molecular Cloning: a Laboratory Manual*, 2nd Edition, eds. Sambrook, et al., Cold Spring Harbor Laboratory Press, (1989), incorporated herein by reference). Cells can be contacted immediately with exogenous DNA or frozen in glycerol or DMSO for subsequent use. Upon thawing to 4° C. and contacting with plasmid DNA, frozen competent cells typically have transformation efficiencies of $1 \times 10^8$-$1 \times 10^{11}$ transformants/µg of plasmid DNA.

Electroporation has also been used to transform cells (see, e.g., Dower et al., Nucleic Acids Research, 16: 6127-6145 (1988); Taketo, Biochimica et Biophysica Acta, 949: 318-324 (1988); Chassy and Flickinger, FEMS Microbiology Letters, 44: 173-177 (1987); and Harlander, Streptococcal Genetics, eds. Ferretti and Curtiss, American Society of Microbiology, Washington, D.C., pp. 229-233 (1987), all incorporated herein by reference). Electroporation methods rely on creating temporary holes in cell membranes by exposing cells to a high voltage electric impulse to facilitate the uptake of exogenous nucleic acids (see, e.g., Andreason and Evans, Biotechniques, 6: 650-660 (1988), incorporated herein by reference). Cells exposed to an electroporation buffer (e.g., 10-15% glycerol) are generally stored by freezing to provide a supply of electrocompetent cells (see, e.g., U.S. Pat. No. 6,004,804, incorporated herein by reference in its entirety). Other methods of preparing competent cells are described, without limitation, in the Examples below.

In yet another embodiment, cells rendered competent for transformation are prepared which contain or express the Cre recombinase, and are repressed in RecBCD activity. As previously noted, Cre recombinase expression can be induced, for example, by means of an inducer if an inducible promoter is used, shortly prior to rendering the cells competent. Likewise, the cells can be repressed in RecBCD activity, for example, by repressing its expression if using a repressible promoter, or by inducing the expression of a RecBCD inhibitor, if driven by an inducible promoter.

Method of Circularizing DNA

In another aspect, the present invention describes a method of circularizing a linear DNA molecule comprising at least two loxP sites. The method comprises introducing the linear DNA molecule into an isolated host cell which transiently expresses the Cre recombinase protein and which is at least transiently repressed for RecBCD activity. The linear DNA molecule is circularized in the cell by the Cre recombinase protein.

The linear DNA molecule is circularized by the site-specific recombination at the two loxP sites. It will be appreciated by those of skill in the art that, in addition to circularizing a single linear DNA molecule, the method described herein can be used to circularize a plurality of linear molecules, each containing at least two loxP sites. Although expected to occur less frequently, site-specific recombination and circularization of a plurality of linear molecules can nevertheless be achieved using the methods described herein, and such events can be identified using methods known in the art (e.g., selection for circularization using selectable markers present on each of the two linear molecules).

In embodiments in which a plurality of DNA molecules is joined and circularized, it is not necessary that all the DNA molecules be introduced into the cell at once. For example, the methods described herein can be used to join two molecules, one of which was already present within the cell. Thus, it is only necessary that one linear DNA molecule be introduced into the cell.

The cells described herein transiently express or contain the Cre recombinase protein. For the methods described herein, it is only necessary that the cells express or contain the Cre recombinase protein at the time that a linear DNA molecule is introduced into the cell.

For the methods described herein, a higher degree of circularization can be achieved by reducing exonuclease activity at the time the linear DNA molecule is introduced into the cell. Circularization methods described herein are enhanced by reducing the exonuclease activities, for example of the RecBCD enzyme. Therefore, in one embodiment, the cell lacks a functional recB gene. In another embodiment, the cell lacks a functional recC gene. In still another embodiment, the cell is transiently repressed for RecBCD activity, in particular at the time that the linear DNA molecule is introduced into the cell.

Kits

Also described herein are kits useful for the circularization of linear DNA molecules. The kit comprises cells described above, and optionally an instruction manual and packaging material therefor. The cells can be provided as competent cells, into which linear DNA molecules can be introduced.

The kit can also comprise primers, buffers, and additional reagents which can be used to generate linear DNA molecules which can be circularized according to the methods described herein.

The following are provided for exemplification purposes only and are not intended to limit the scope of the invention described in broad terms above. All references cited in this disclosure are incorporated herein by reference.

EXAMPLES

Example 1

Inter-Molecular Ligation and Molecular Cloning Using Univalent Topoisomerase-Bound DNA An insert nucleic acid molecule, for example, a PCR product, can be generated by PCR using a primer set consisting of a 5'-primer and 3'-primer. Two vector nucleic acid molecules, for example, a left vector arm and a right vector arm are prepared such that a topoisomerase enzyme (TOPO) is covalently bound only to one end of a nucleic acid molecule to form a univalent topoisomerase vector molecule. PCR primers for generating an insert molecule can be synthesized to possess either a hydroxyl group or phosphate group at each of the 5'-ends. A hydroxyl group permits ligation to topoisomerase-bound DNA while a phosphate group prohibits such ligation.

For non-directional ligation of a PCR insert molecule to, for example two vector arms, both PCR primers will possess 5'-hydroxyl groups. The PCR insert can ligate with the vector arms to form four different types of ligation products: 1) left vector arm (LVA)-insert molecule (I)-left vector arm (LVA); 2) right vector arm (RVA)-insert (I)-right vector arm (RVA); 3) LVA-I-RVA; and 4) RVA-I-LVA. Only the LVA-I-RVA and RVA-I-LVA create viable replication competent entities (FIG. 1).

Figure 2:
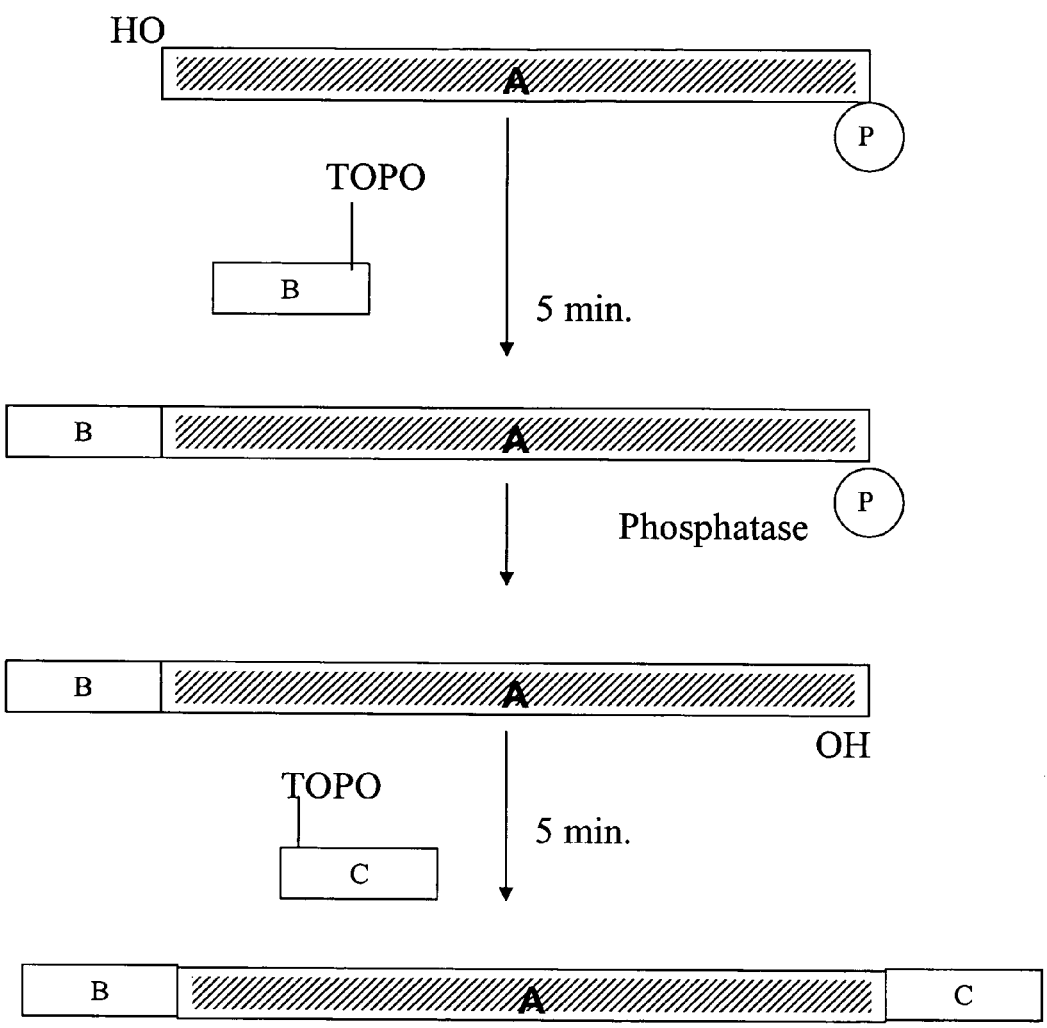
FIG. 2 shows the directional covalent joining of an insert molecule with a 5'—OH group on one end and a 5'-phosphate group on the other end to a right vector arm and a left vector arm each comprising a topoisomerase polypeptide on one end only.

For directional ligation of a PCR insert molecule to, for example, left and right vector arms, one PCR primer possesses a 5'-hydroxyl group and the other PCR primer possesses a 5'-phosphate group. The PCR generated insert molecule is generated and is first ligated to one vector arm, for example, a LVA to create a LVA-I-5'-phosphate molecule. The 5'-phosphate end of this molecule is unable to ligate to the LVA or RVA because the vector arm sites to which the TOPO is bound contain a 3'-phosphate. This molecule is then dephosphorylated to create to LVA-I-5'—OH. The LVA-I-5'—OH molecule is then ligated to the other vector arm (RVA) to form LVA-I-RVA (FIG. 2). Once the ligated insert/vector molecule described above has been constructed, the two vector arms can be non-covalently or covalently joined to one another, at the ends distal to the covalently attached topoisomerase polypeptide (i.e., their free ends), by a number of methods such that a circular molecule is formed. Such methods include, for example, ligase enzyme mediated ligation, complementary sequence annealing, topoisomerase mediated ligation, in vitro or in vivo site-specific recombination, or in vivo homologous recombination.

Example 2

Directional Molecular Cloning Using Topoisomerase and a Ligase Enzyme

Figure 3:
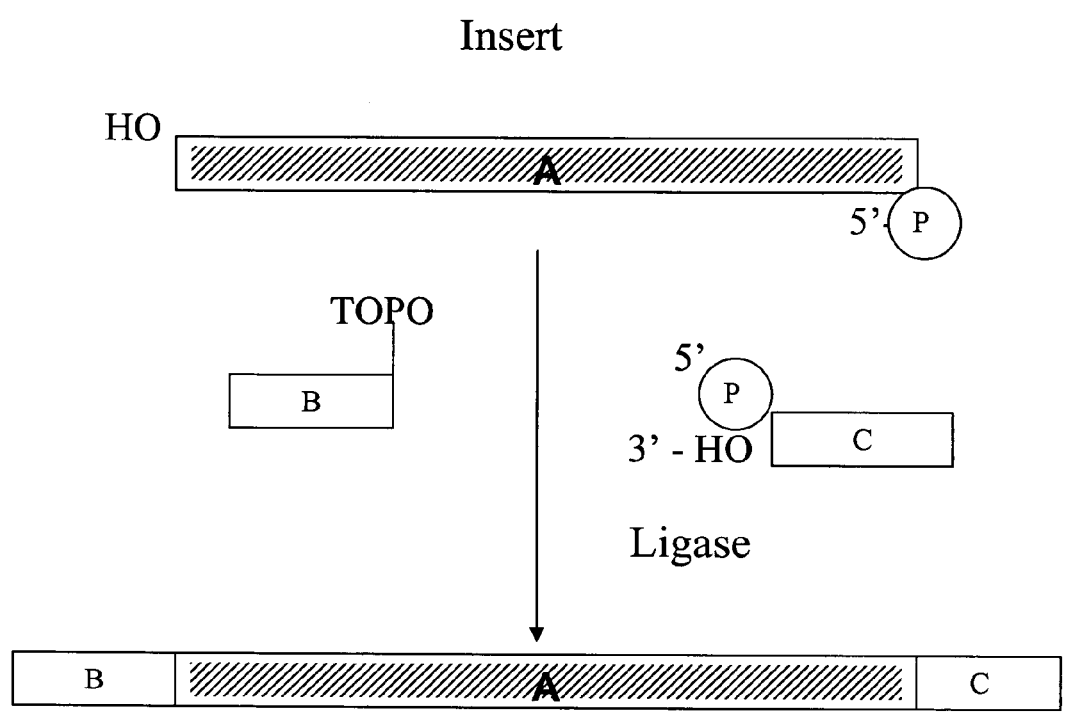
FIG. 3 shows the directional covalent joining of an insert molecule with a 5'—OH group on one end and a 5'-phosphate group on the other end to a left vector arm comprising a topoisomerase polypeptide on one end only and a right vector arm comprising a ligation substrate site on one end.

A nucleic acid insert is generated using, for example, a pair of PCR primers wherein one primer (P1) has a hydroxyl group at its 5'-end (OH-P1) and the other primer (P2) has a phosphate group at its 5'-end (P2-P) (see FIG. 3). The insert molecule is generated by PCR. A linear vector nucleic acid is prepared such that it has TOPO bound at one end (univalent TOPO-bound nucleic acid molecule); the other end of the linear vector nucleic acid comprises a substrate for ligation (a 3'—OH) to be mediated by a ligase enzyme. In a single incubation, the PCR insert can be ligated to the TOPO-end of the linear vector nucleic acid via TOPO-mediated ligation and to the other end of the linear vector nucleic acid via a ligase enzyme-mediated reaction. The product of the ligation is transformed into an appropriate host cell. A cloning event mediated by both topoisomerase and DNA ligase is unidirectional. The hydroxyl or phosphate group at the 5'-end of the PCR primers determines the directionality of the insert.

A second approach involving a topoisomerase- and ligase-mediated ligation comprises generation of an insert by for example, PCR. Where PCR is used to generate an insert, a pair of PCR primers where one has a hydroxyl group at its 5'-end (HO-P1) and the other has a phosphate group at its 5'-end (P2-P) (see FIG. 4). A vector, such as two vector nucleic acid arms, can be prepared such that one vector arm has a TOPO bound at one end (univalent TOPO-bound DNA molecule) and the other vector arm has a substrate for ligation at one end. In a single incubation, the PCR insert is ligated to the one vector arm with a TOPO end via TOPO-mediated ligation and to the other vector arm with the ligation-ready end via ligase enzyme-mediated reaction. The product of the ligation is transformed into an appropriate host cell. The cloning event mediated by both topoisomerase and DNA ligase is unidirectional. The hydroxyl or phosphate group at the 5'-end of the PCR primers determines the directionality. The other ends of the two vector arms are then joined by any of the methods described above. Using this cloning method the ligation products comprised of RVA-I-RVA or LVA-I-LVA should not be formed, but in the event that some do occur, such ligation products are incapable of subsequent replication and propagation.

Example 3

Molecular Cloning Using Topoisomerase and cos Ends

Figure 5:
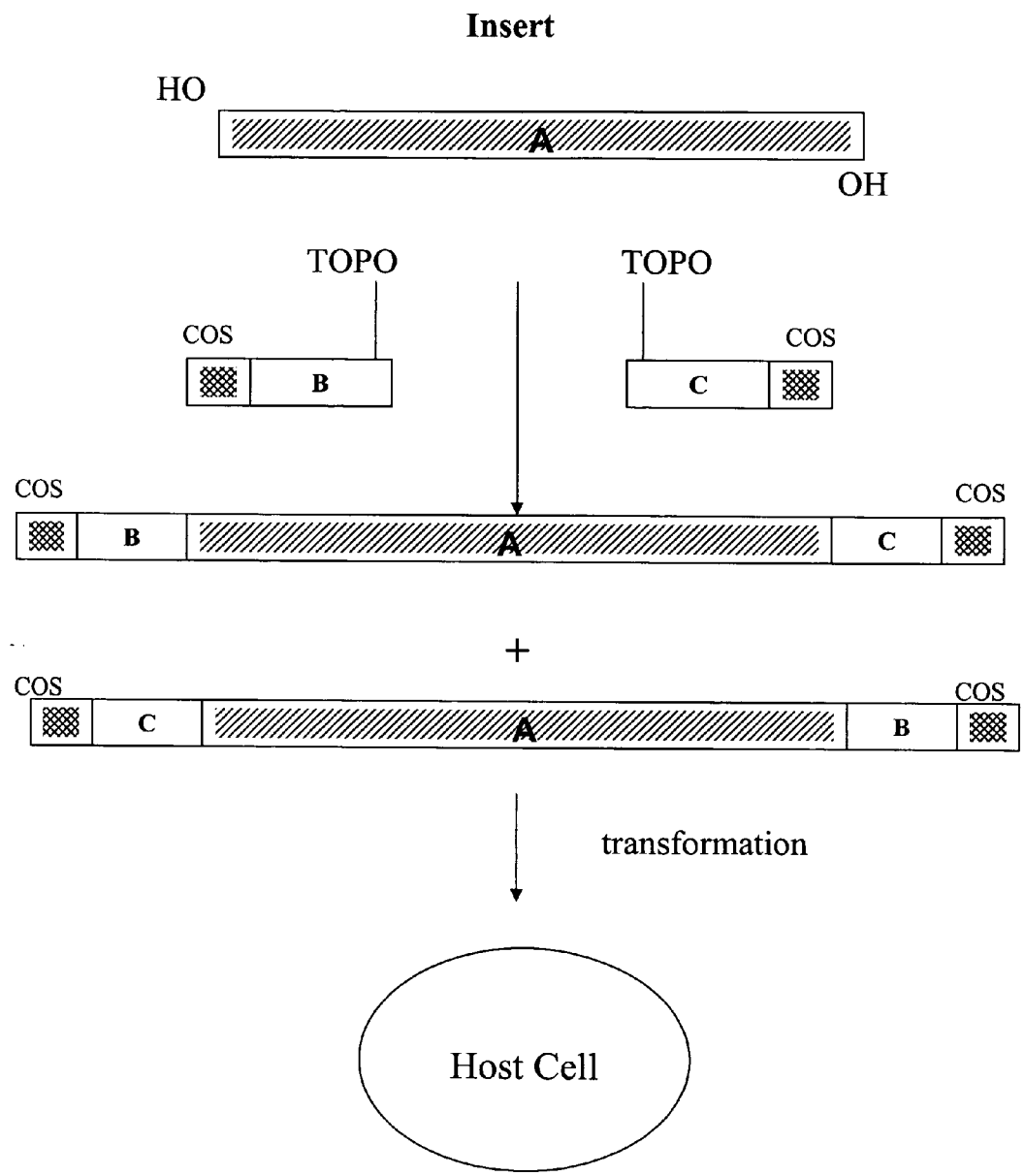
FIG. 5 shows the non-directional cloning of an insert molecule with 5'—OH groups on each end to a right vector arm and a left vector arm each comprising a topoisomerase polypeptide on one end only and a cloning substrate site, cos, on the other end.

A method of molecular cloning using topoisomerase and cos ends can comprise a vector, where such a vector may consist of two vector arms, with each arm consisting of one TOPO-end and one cos end. cos refers to the cohesive ends present at the termini of bacteriophage lambda. An insert, such as a PCR insert, can be generated using primers comprising 5'—OH termini. The PCR insert can be ligated to a TOPO-end of the two vector arms by DNA topoisomerase (see FIG. 5). Ligation events that result in LVA-I-LVA or RVA-I-RVA cannot subsequently be propagated. The product of the ligation can be transformed into a suitable host. The distal ends of the vector arms contain terminal cos sites that are readily annealed to one another in E. coli host cells by virtue of their explicit sequence. cos sites do not anneal in vitro at room temperature.

Figure 6:
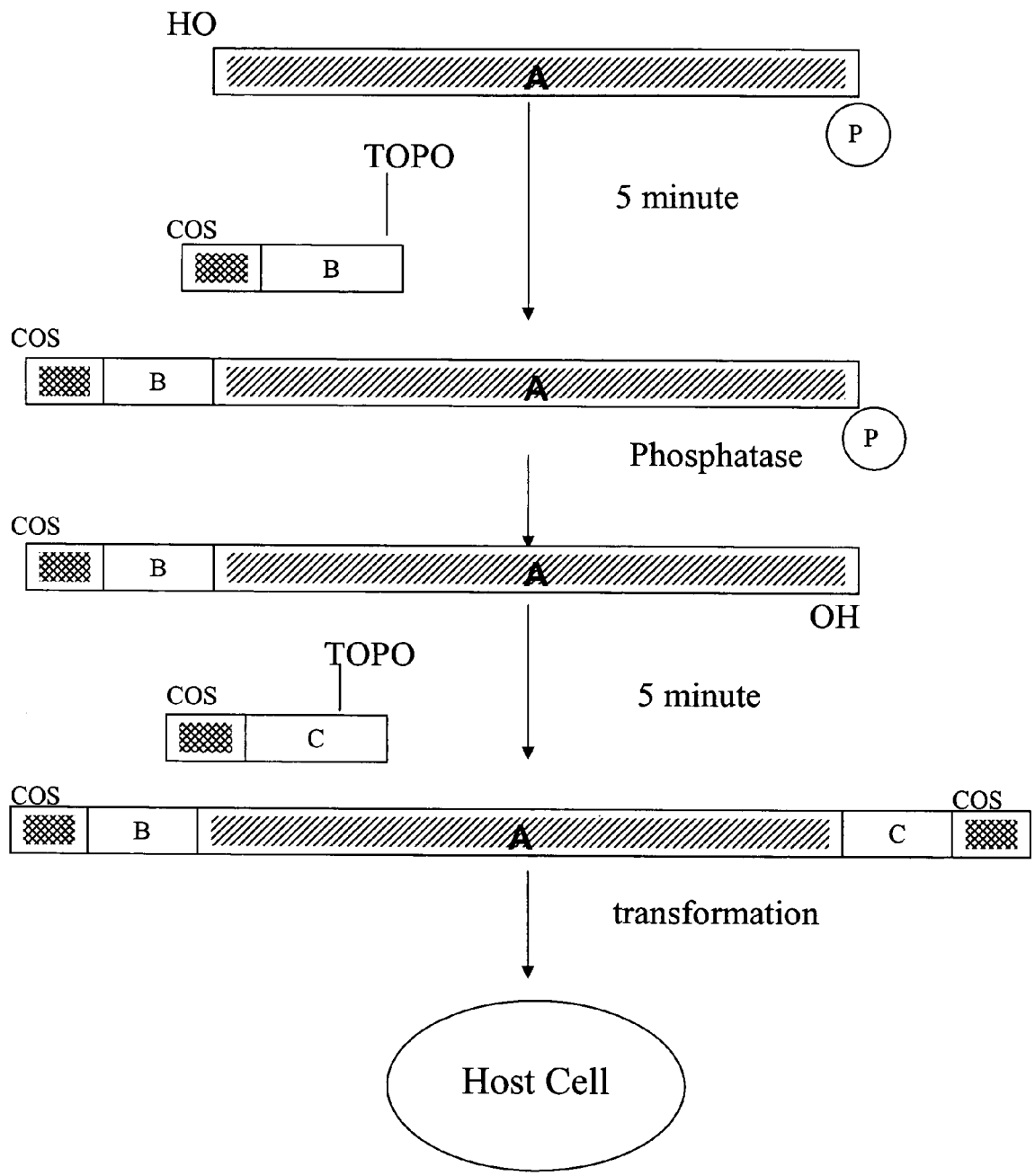
FIG. 6 shows the directional cloning of an insert molecule with a 5'—OH group on one end and a 5'-phosphate group on the other end to vector molecules comprising a topoisomerase polypeptide on one end only and a cloning substrate site, cos, on the other end.

This method of cloning can be directional or non-directional. In the case of non-directional cloning, an insert comprises a 5'-hydroxyl ends and can be ligated to, for example, two vector arms in a single reaction. For directional cloning, an insert can be generated by, for example, PCR wherein one PCR primer has a 5'-hydroxyl group and the other PCR primer has a 5'-phosphate group. Thus, the resulting PCR insert will contain one 5'-hydroxyl end and one 5'-phosphate end. The insert is to be ligated sequentially, first to a left vector arm containing a TOPO bound end followed by dephosphorylation of the 5'-phosphate of the insert and then ligation to the right vector arm containing a TOPO bound end (FIG. 6).

The ligation product of the insert to the vector is a linear molecule in vitro with two cos sequences at its end. It is transformed into a host, such as E. coli more efficiently than a circular molecule.

Example 4

Molecular Cloning Using Topoisomerase and LIC Ends

Figure 7:
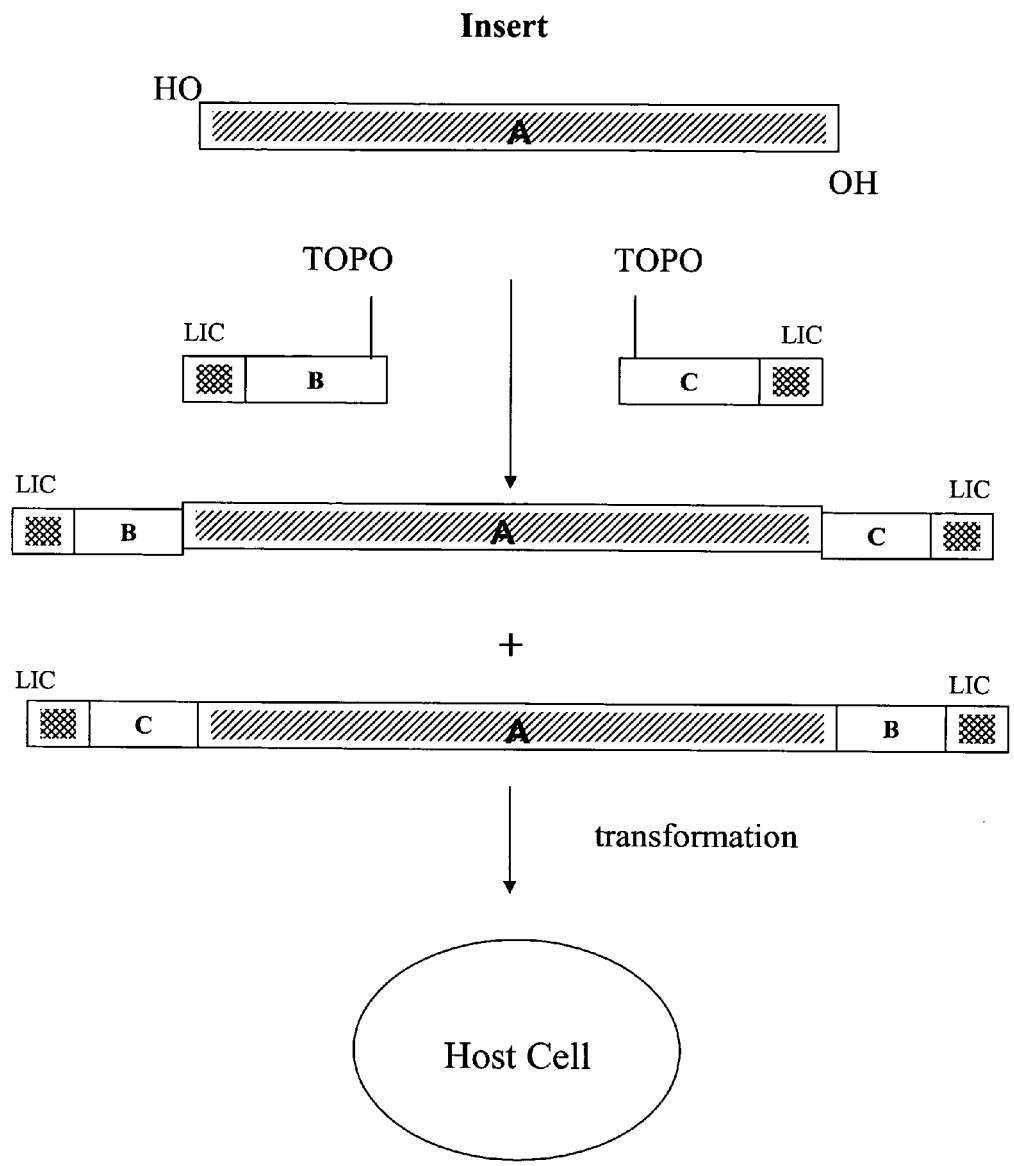
FIG. 7 shows the non-directional cloning of an insert molecule with 5'—OH groups on each end to a right vector arm and a left vector arm each comprising a topoisomerase polypeptide on one end only and a cloning substrate site, LIC, on the other end.

A method of molecular cloning using topoisomerase and LIC ends can comprise a vector, such as two vector arms, each consisting of one TOPO-end and one LIC end. An insert, such as a PCR insert, can be generated using primers comprising two 5'—OH termini. The PCR insert can be ligated to a TOPO-end of the two vector arms by DNA topoisomerase (see FIG. 7). Ligation events that result in LVA-I-LVA or RVA-I-RVA cannot subsequently be propagated. The distal ends of the vector arms contain terminal LIC sites that are readily annealed to a plasmid comprising LIC compatible ends.

Figure 8:
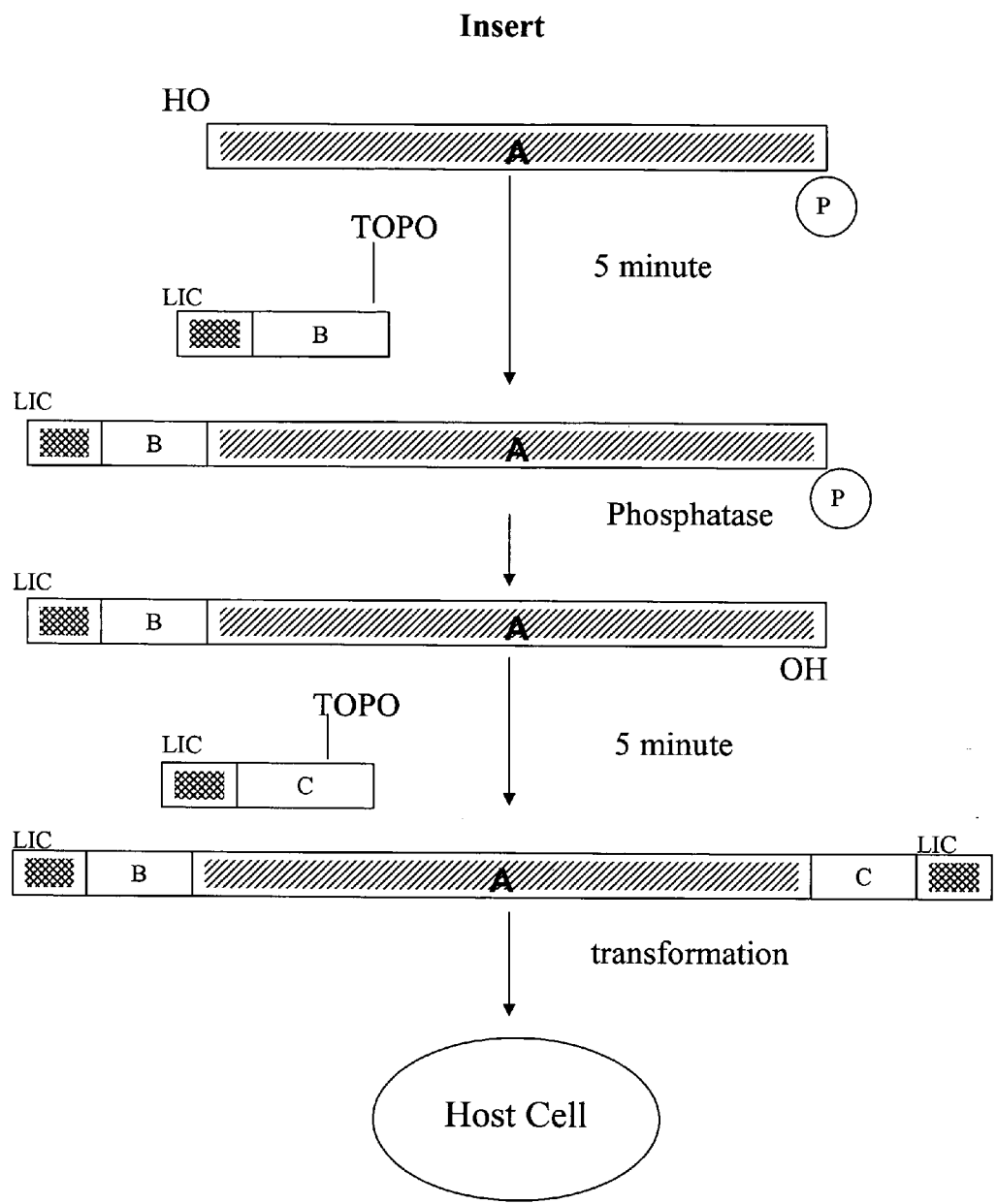
FIG. 8 shows the directional cloning of an insert molecule with a 5'—OH group on one end and a 5'-phosphate group on the other end to vector molecules comprising a topoisomerase polypeptide on one end only and a cloning substrate site, LIC, on the other end.

This method of cloning can be directional or non-directional. In the case of non-directional cloning, an insert comprising 5'-hydroxyl ends and can be ligated to, for example, two vector arms in a single reaction. For directional cloning, an insert can be generated by, for example, PCR wherein one PCR primer has a 5'-hydroxyl group and the other PCR primer has a 5'-phosphate group. Thus, the resulting PCR insert will contain one 5'-hydroxyl end and one 5'-phosphate end. The insert is to be ligated sequentially, first to the left vector arm containing a TOPO bound end and followed by dephosphorylation of the 5'-phosphate of the insert and then ligation to the right vector arm containing a TOPO bound end (FIG. 8).

Example 5

Molecular Cloning into Lambda Vector

Figure 9:
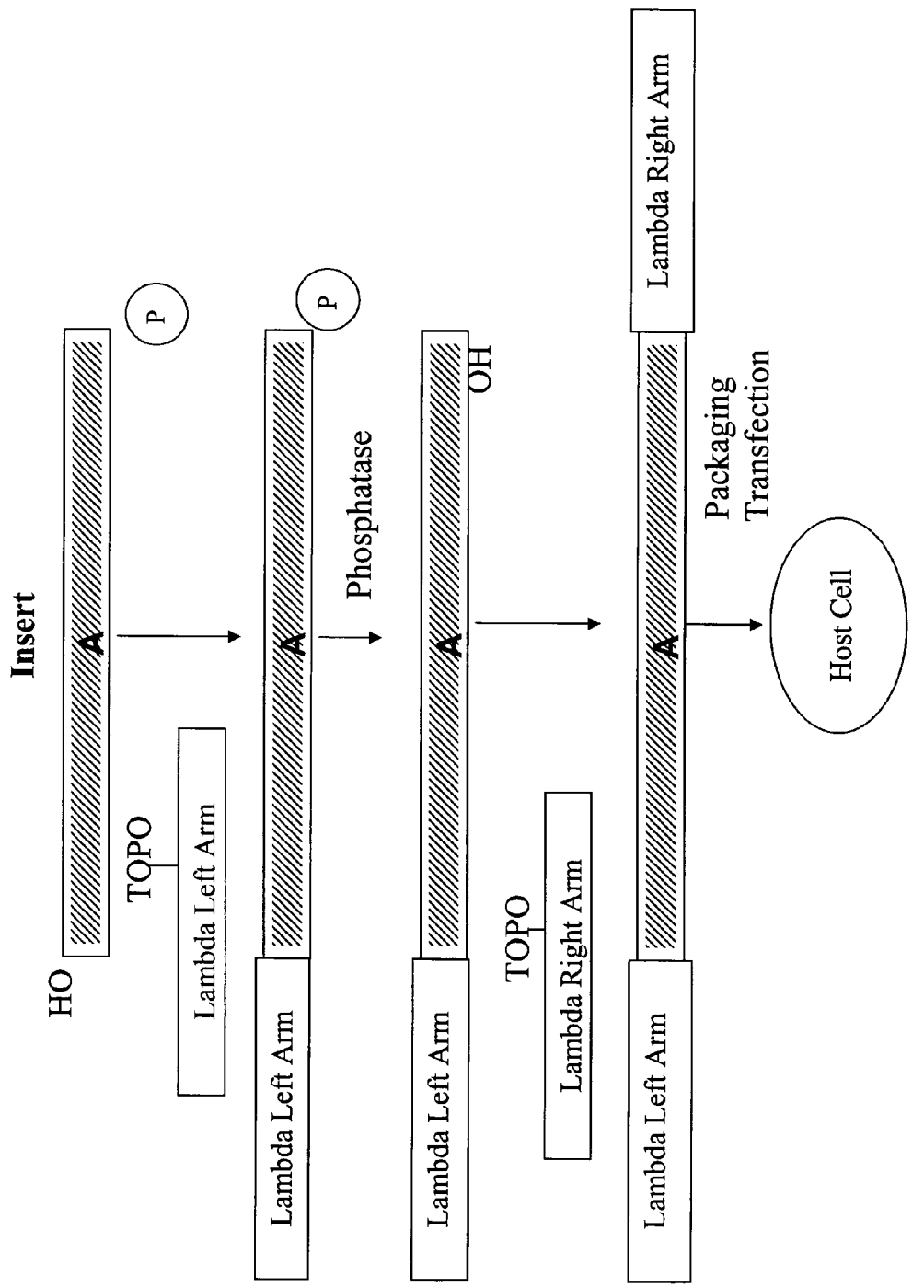
FIG. 9 shows the directional cloning of an insert molecule with a 5'—OH group on one end and a 5'-phosphate group on the other end to vector molecules comprising a topoisomerase polypeptide on one end only of a lambda vector arm.

The vector can comprise lambda DNA vector arms (termed left lambda arm (LLA)) and right lambda arm (RLA)). An insert, such as a PCR generated insert, can be ligated to the lambda vector arms in a directional manner or non-directional manner. In the case of non-directional cloning, a PCR insert can be generated using 5'-hydroxyl PCR primers. The insert can be ligated to two lambda vector arms in a single reaction. Ligation events resulting in LLA-I-LLA or RLA-I-RLA cannot subsequently be propagated. For directional cloning, one PCR primer has a 5'-hydroxyl end and the other PCR primer has a 5'-phosphate end. Thus, the PCR insert is comprised of one 5'-hydroxyl end and one 5'-phosphate end. The insert can be ligated sequentially to the two lambda vector arms with a dephosphorylation step in between as depicted in FIG. 9. The ligated lambda construct can be packaged in vitro and transfected into host cells such as XLI-Blue E. coli. A circular plasmid DNA containing the insert of interest can be rescued from the lambda vector using, for example, ZAP technology (Stratagene).

Example 6

Molecular Cloning Into a Linear Plasmid DNA Molecule

Figure 10:
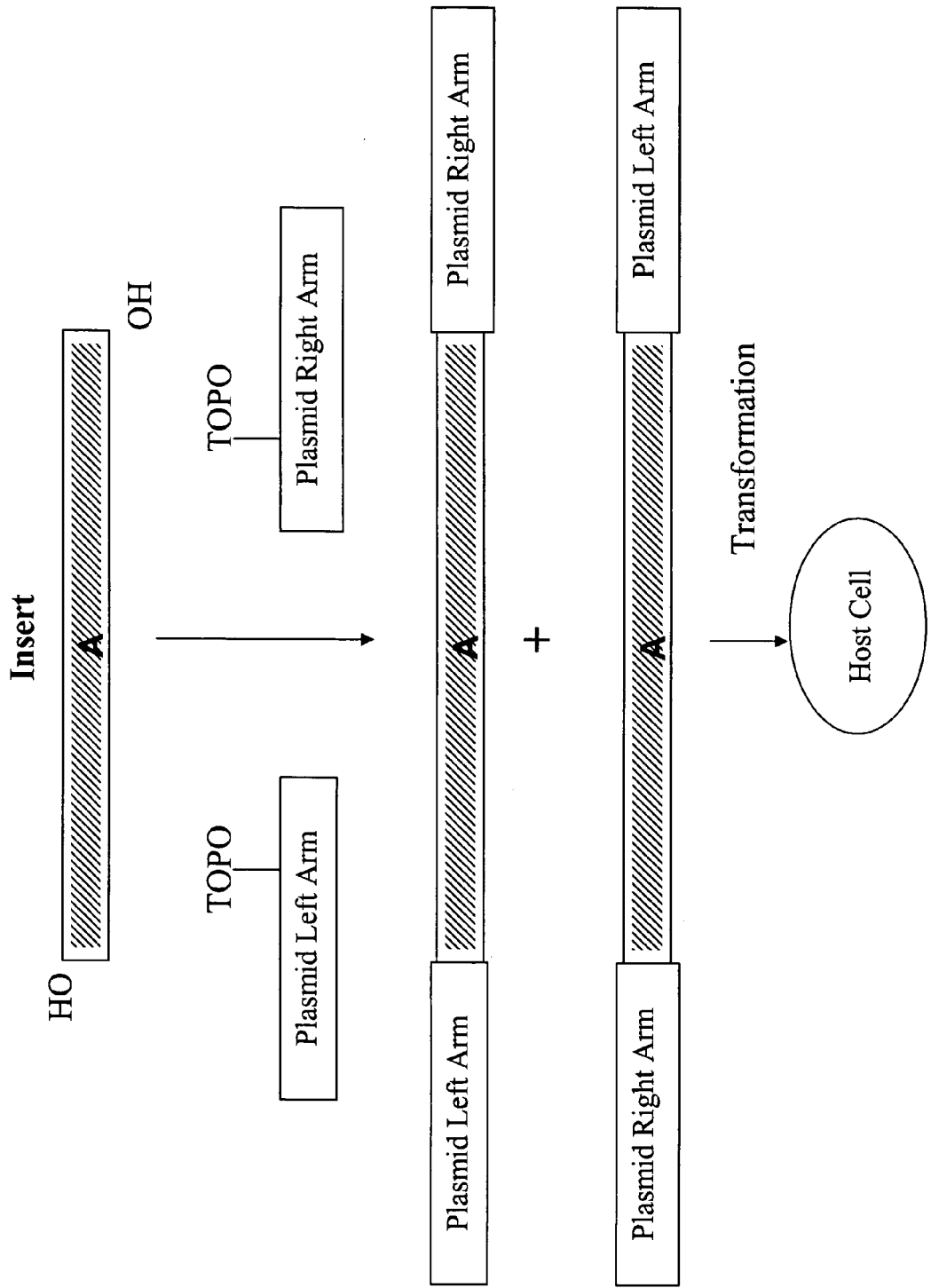
FIG. 10 shows the non-directional cloning of an insert molecule with 5'—OH groups on each end to a right plasmid arm and a left plasmid arm each comprising a topoisomerase polypeptide on one end only.
Figure 11:
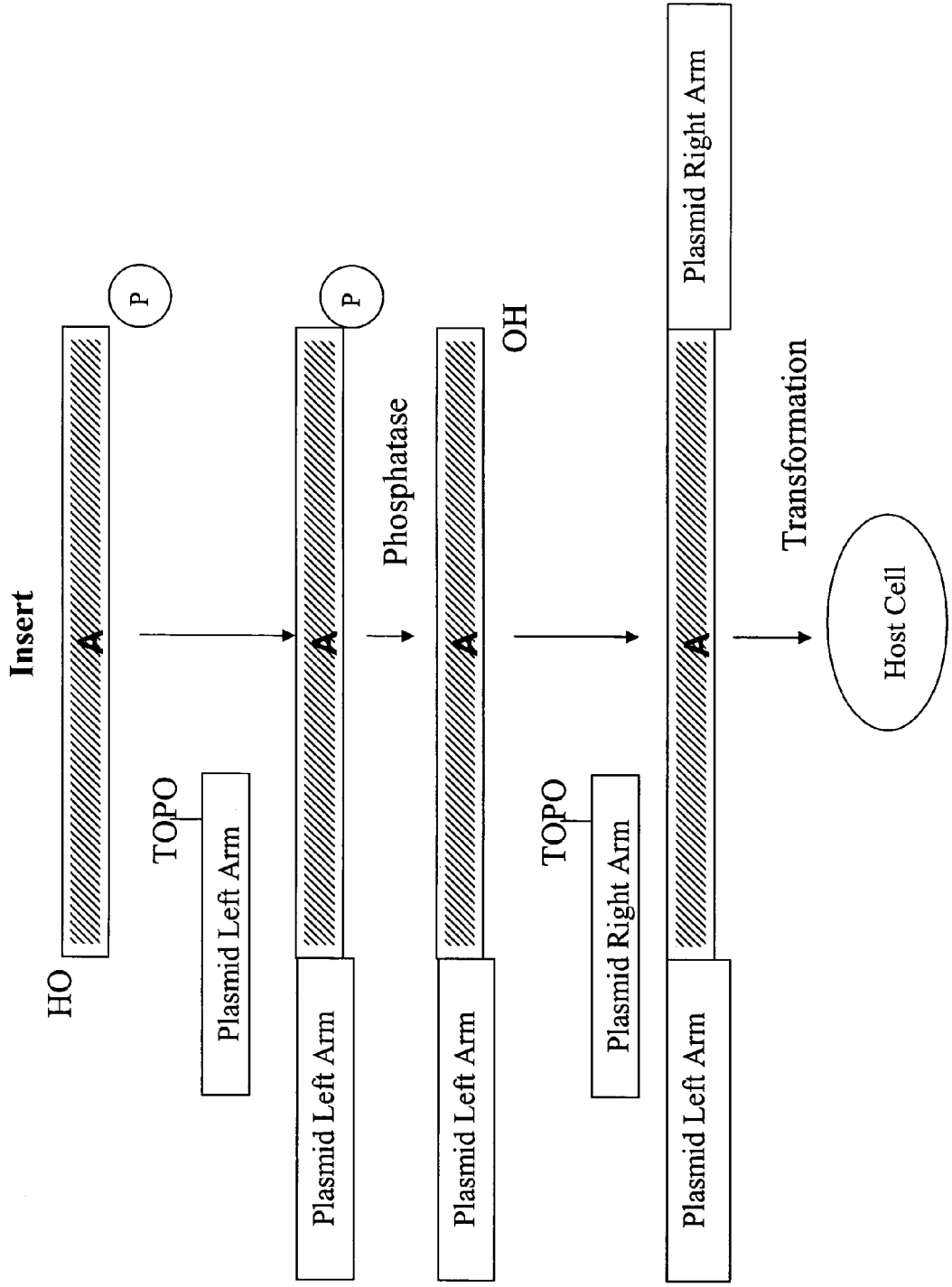
FIG. 11 shows the directional cloning of an insert molecule with a 5'—OH group on one end and a 5'-phosphate group on the other end to vector molecules comprising a topoisomerase polypeptide on one end only.

A vector can comprise vector arms of a linear plasmid such as N15. An insert, such as a PCR generated insert, can be ligated to the plasmid vector arms in a directional manner or non-directional manner. In the case of non-directional cloning, a PCR insert can be generated using 5'-hydroxyl PCR primers. The insert can be ligated to two plasmid vector arms in a single reaction (FIG. 10). Ligation events resulting in LVA-I-LVA or RVA-I-RVA cannot subsequently be propagated. For directional cloning, one PCR primer has a 5'-hydroxyl end and the other PCR primer has a 5'-phosphate end. Thus the PCR insert is comprised of one 5'-hydroxyl end and one 5'-phosphate end. The insert can be ligated sequentially to the two plasmid vector arms with a dephosphorylation step in between as depicted in the FIG. 11. The linear DNA can be transformed directly into E. Coli. Alternatively, the ligated plasmid construct can be packaged in vitro and transfected into host cells such as XLI-Blue E. coli. A DNA containing the insert of interest can be rescued from the vector using, for example, ZAP technology (Stratagene).

Figure 4:
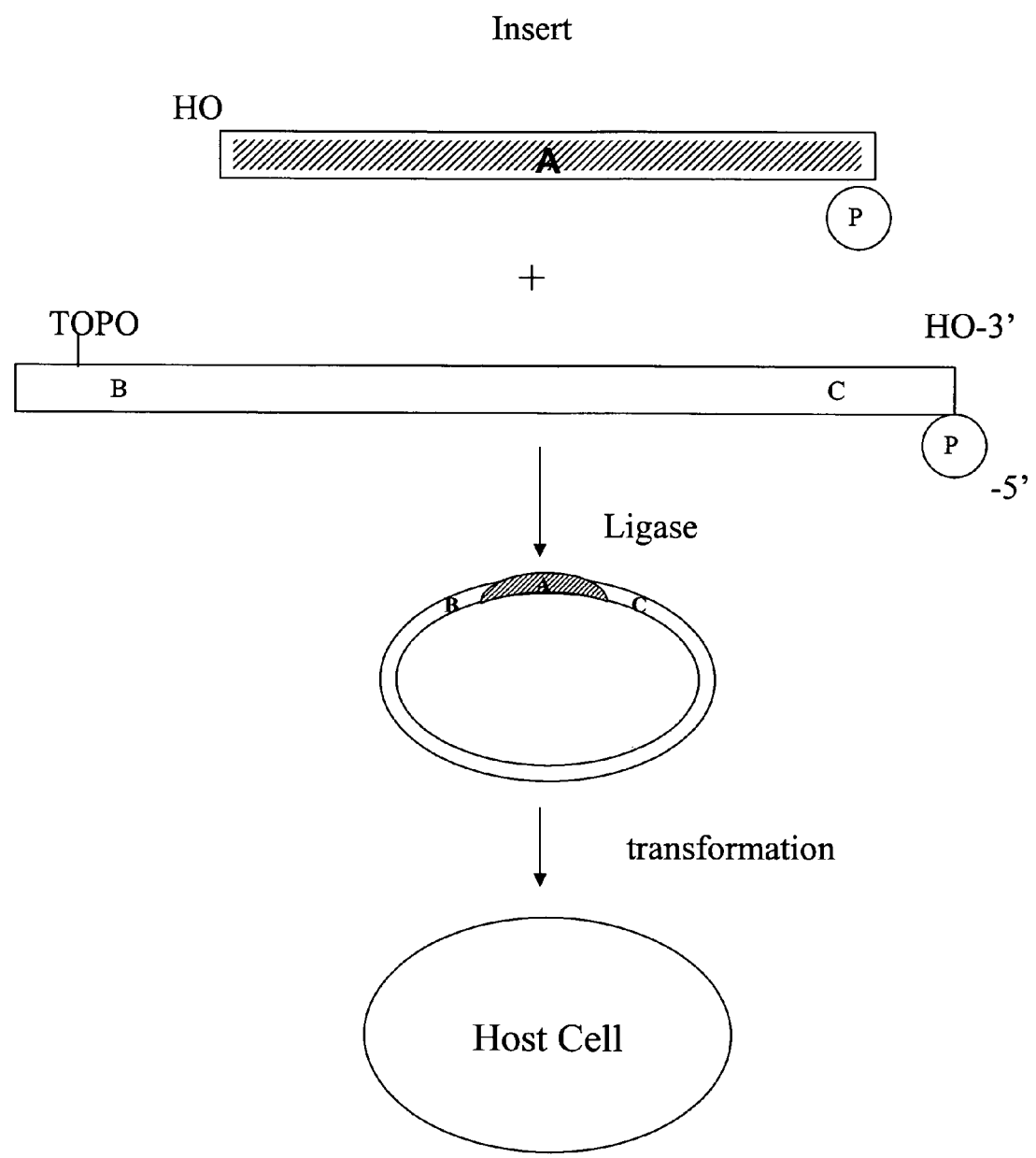
FIG. 4 shows the directional cloning of an insert molecule with a 5'—OH group on one end and a 5'-phosphate group on the other end to a linear vector molecule. The linear vector molecule comprises a topoisomerase molecule on one end only and a ligation substrate site on the other end.

A vector can also comprise a linear plasmid vector consisting of a covalently bound topoisomerase polypeptide at one end and a ligation substrate site at the other end (see FIG. 4). Incubation of the vector with an insert molecule comprising 5'—OH group on one end and a 5'-phosphate group on the other end, under conditions sufficient for topoisomerase-mediated ligation and ligase enzyme-mediated ligation results in a ligated circular plasmid comprising the insert molecule. The plasmid can be transformed into a host cell.

Example 7

Molecular Cloning Using Topoisomerase and Site-Specific Recombination

Figure 12:
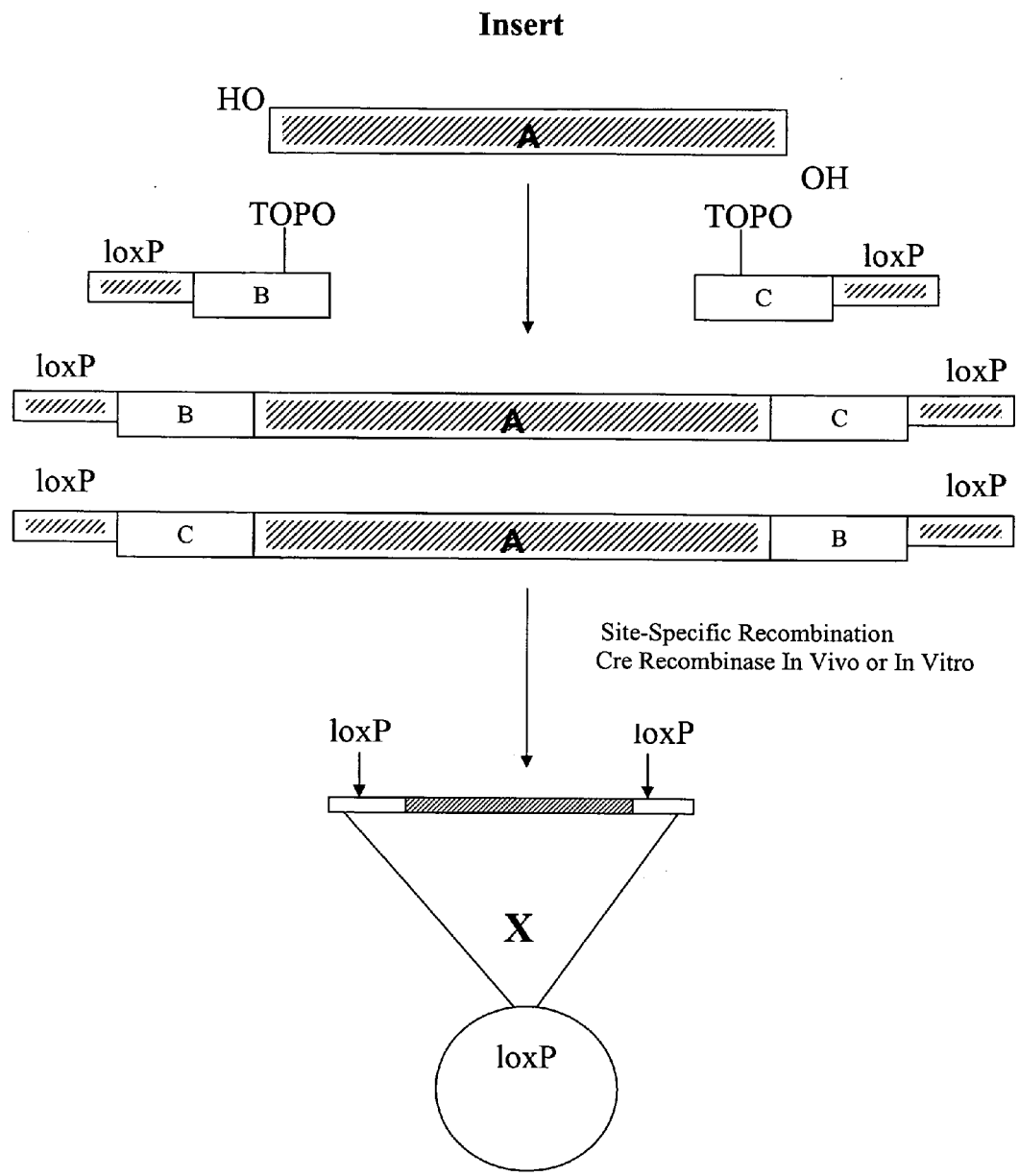
FIG. 12 shows the non-directional cloning of an insert molecule with 5'—OH groups on each end to a right vector arm and a left vector arm each comprising a topoisomerase polypeptide on one end only and a cloning substrate site, a loxP site, on the other end.
Figure 13:
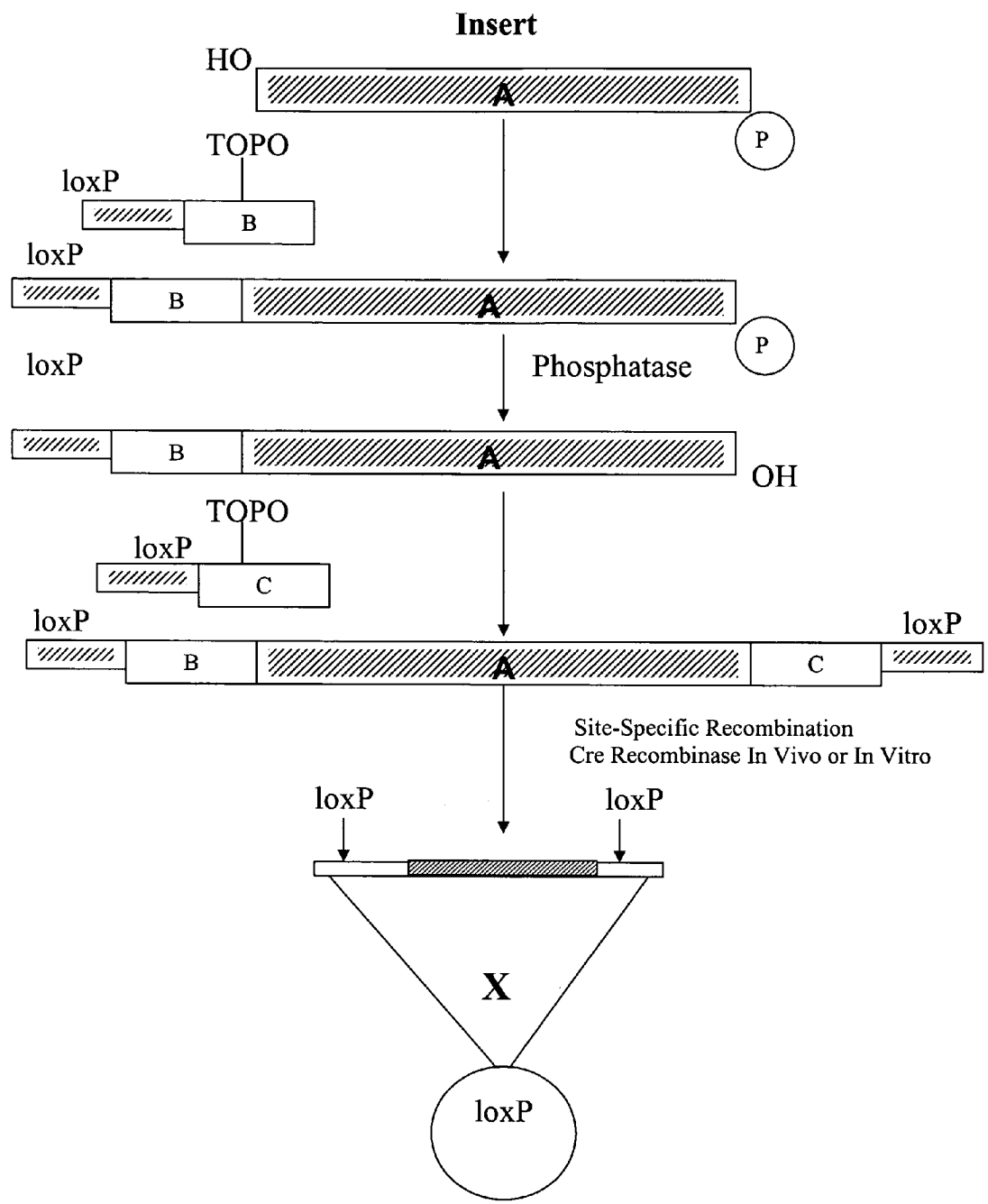
FIG. 13 shows the directional cloning of an insert molecule with a 5'—OH group on one end and a 5'-phosphate group on the other end to vector molecules comprising a topoisomerase polypeptide on one end only and a cloning substrate site, a loxP site, on the other end.

A vector can comprise vector arms that comprise one TOPO-end and one loxP end. The loxp site can be recombined with a second loxP site in the presence of a Cre site-specific recombination protein. An insert, such as a PCR generated insert, can be ligated to the TOPO-end of the two vector arms. Such cloning can be directional or non-directional. In the case of non-directional cloning, an insert, such as a PCR insert can be generated from PCR primers each comprising 5'-hydroxyl ends. An insert comprising two 5'—OH ends can be ligated to two vector arms in a single reaction (FIG. 12). For directional cloning, an insert can be generated by, for example, PCR wherein one PCR primer comprises a 5'-hydroxyl end and the other PCR primer comprises 5'-phosphate end resulting in an insert that comprises one 5'-hydroxyl end and one 5'-phosphate end. The insert can be ligated sequentially to two vector arms with a dephosphorylation step in between as depicted in FIG. 13. The ligation product comprises a loxP site at each end of a linear molecule. The linear molecule can be recombined into a circular recombinant plasmid in vitro, for example using purified Cre recombinase or in vivo by, for example transformation into an E. coli host expressing Cre recombinase and a plasmid that has loxP sites.

Example 8

Molecular Cloning Using Topoisomerase and Homologous Recombination in Vivo

Figure 14:
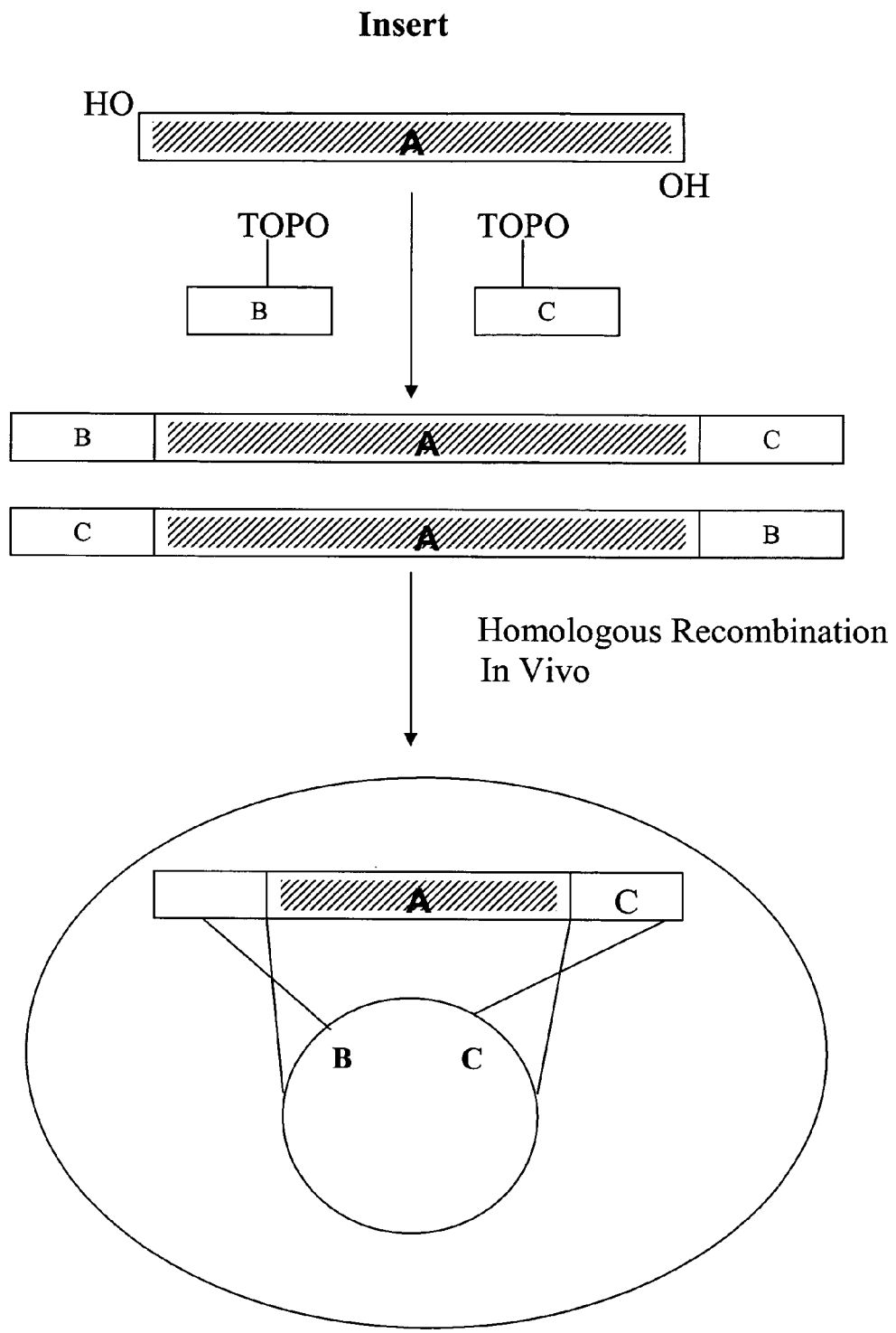
FIG. 14 shows the non-directional cloning of an insert molecule with 5'—OH groups on each end to a right vector arm and a left vector arm each comprising a topoisomerase polypeptide on one end only and a cloning substrate site, a site for homologous recombination, on the other end.

In vivo homologous recombination can be exploited to transfer a ligated insert/vector of interest into a circular plasmid vector. Homologous sequences flank a ligated insert/vector of interest and are substantially identical to sequences of a plasmid cloning vector. A ligated insert/vector of interest is recombined into a plasmid cloning vector of choice via homologous recombination between the homologous sequences flanking the ligated insert/vector and in the plasmid cloning vector. An insert can be generated with homologous sequences attached to each end by, for example, synthesizing PCR primers with homologous vector sequences, of for example, 30, 75, 100, 150, 200, 250, 500, or 1000 base pairs and using the PCR primers to generate a ligated insert/vector with homologous vector sequences flanking the ligated insert/vector of interest. A ligated insert/vector molecule with homologous sequences at the ends can also be generated by preparing topoisomerase-bound homologous sequence elements and employing a TOPO cloning scheme as outlined in FIGS. 14 and 15 for generating an insert with homologous sequence elements on each end. A PCR amplified insert containing TOPO ligated arms can be transformed into host cells containing a cloning vector wherein homologous recombination can occur. For efficient in vivo homologous recombination, a recA+ host strain can be used. To protect a linear insert from degradation by endogenous exonuclease activities, the ends of the insert can be modified to either inhibit or prohibit exonuclease digestion events.

To achieve site-specific in vivo recombination, lambda attachment sites can be employed in place of the homologous sequences described above. In this scenario, lambda attachment sites flank a ligated insert/vector of interest, which is generated according to the PCR and TOPO cloning schemes described above. The ligated insert/vector with the flanking lambda attachment sites is transformed into host cells containing a cloning vector with lambda attachment sites. Inside the host cell, the ligated insert/vector then can be site-specifically recombined into a plasmid cloning vector between the lambda attachment sites flanking the ligated insert/vector and those sites in the plasmid cloning vector.

Example 9

Generation of Strains (Methods)

A. Preparation of Recombination Cassette by PCR

120/122 targeting fragment: this PCR fragment has a cre recombinase gene with a Chloramphenicol resistance (CAM) marker flanked by FRT sites. There is a 78 bp 5' homology armn to the AraB promoter with 1 nucleotide deleted, which results in a better ribosomal binding site and a 89 bp fragment homologous to the araD gene. The cassette was assembled with the EasyA enzyme blend (Stratagene #600404) using outer primers BB110 and 113 and 10 fold diluted inner primers BB 111 and 112 using pACYC-Cre and pKSF-Cam as template. To add longer homology arms this 110/113 product was reamplified using primers BB120 and 122.

Figure 19:
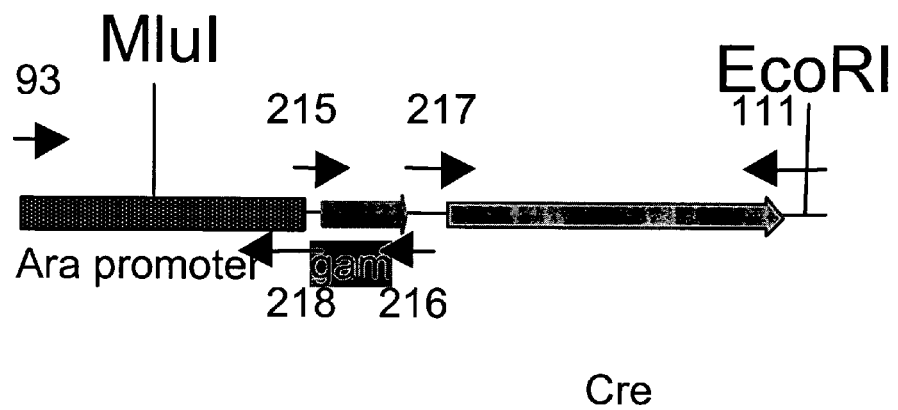
FIG. 19 shows the strategy for cloning the gam recBC inhibitor upstream of the cre cassette by overlapping PCR, using outer primers BB093 and BB111 and inner primers BB215, 216, 217, and 218.

B. Vectors with Recombination Cassettes pUC18-98-128: insertion site of araBA-cre vector in from E. coli strain BW#3 amplified by EasyA with BB128/098 and cloned into PvuII cut T-tailed pUC18.

pUC18 ara-cre V3.0: Changed RBS in pUC18-98-128 and mutated a putative promoter at the ara/cre junction, inverted Cam cassette. 2 PCR fragments were generated: 1. Using primers BB93 and 111 and 10 fold diluted bridging primer BB133 and 134 with sure cells and pACYC-cre as template; PCR product was digested with MluI and EcoRI 2. Using primer BB 131 and 132 to amplify Cam cassette from pKSF-Cam, cut with BglII and EcoRI. Both fragments were cloned into MluI/BglII cut pUC18-98-128. A 3.7 kb AflII-BstXI fragment can be isolated from this plasmid for targeting.

pUC18 ara-cre V3.0 GTG: Changed the ATG start codon of cre with GTG by a QuikChange reaction using primers BB141GTG and 142GTG pUC ara-gam-cre: cloned gam recBC inhibitor upstream of the cre cassette by overlapping PCR assembly. Briefly, a cassette was assembled using outer primers BB093 and BB111 with 10-fold diluted inner primers BB215, 216, 217, and 218 (FIG. 19) using XL-1 cells, pKD46 and pACYC-cre plasmids as template. This PCR fragment was cut with MluI and EcoRI and used to exchange the corresponding fragment in pUC18 ara-cre V3.0. The RBS for the gam cassette was optimized based on the deletion of a T at position −12 in the ara promoter to generate as consensus RBS. In addition, GTG was kept as a start codon for Cre and the start codon also is incorporated into a PmlI site for future cloning purposes. An MluI/BstXI fragment was used for recombination.

C. Bacterial Strains

Cre Expressing *E. coli* or pKD46I into Sure or Sure-derived strains. It was noted that the red genes in pKD46 can be induced with L-Arabinose despite those cells being ara+. An ON culture in NZY/Amp was diluted 1:100 and grown to OD 600 of 0.6 in NZY. pKD46 strains were induced with 10 mM L-Ara for 15 minutes and pKD46I strains with 1 mM IPTG for 15 minutes. Cells were spun down and was 5 times with 20 cell volumes water and taken up in 1/100 of the original culture volume in 10% glycerol in water. Cells can be frozen at −80° C. or 40 µl are used fresh for Electroporation with 50 to 100 ng of PCR targeting product or gelisolated plasmid insert. Cuvettes with a 1 mm gap were used at 1700 V, 25 µF, and 200 Ohms. Cells

| | | | | verfication of correct integration | | | |
|---|---|---|---|---|---|---|---|
| Bacterial Strain | Pedigree | genotype | primer pair | size of PCR product | primer pair | wt PCR product |
| Sure:cre | Sure | carries pACYC-cre, constitutive cre recombinase expression | | | | |
| BW ara/cre#3 | BW25113 | cre driven by araB promoter with good RBS | 117/118 | 507 | 117/121 | 686 |
| Sure ara/cre #1, 2 and 3 | Sure | P1 transfer of ara locus from BW ara/cre#3 | 117/118 | 507 | 117/121 | 686 |
| BW ara-cre clones 2.1, 2.2 and 12.2 | BW25113 | cre driven by araB promoter with weak RBS | 140/118 | 1434 | 117/140 | 1613 |
| Sure V3.0 GTG clone 5 | Sure | Cre driven by ara promoter, weak RBS and GTG start | 140/118 | 1434 | 117/140 | 1613 |
| Sure 3.2.5.8 | Sure V3.0 GTG clone 5 | Cre driven by ara promoter, weak RBS and GTG start, Cam sensitive | 140/118 | 1127 | nd | nd |
| sure 3.2.5.66 | Sure V3.0 GTG clone 5 | Cre driven by ara promoter, weak RBS and GTG start, Cam sensitive | 140/118 | 1127 | nd | nd |
| DH10B:cre clone 8.1 | DH10B | P1 transfer of ara locus from Sure V3.0 GTG clone 5 | 140/118 | 1127 | nd | nd |
| DH10B:cre 812 | DH10B:cre clone 8.1 | Cam selection marker and all plasmids cured | 140/118 | 1127 | nd | nd |
| DH10B:ara-gam-cre | DH10B:cre 812 | Ara B promoter driven gam and cre with GTG on one operon | 117/118 | 900 | nd | nd |
| DH10B:ara-gam-cre 20 StrataClone Cells | DH10B:ara-gam-cre | Ara B promoter driven gam and cre with GTG on one operon, Cam-sensitive | 117/118 | 900 | nd | nd |

Colonies from the recombineering events were screened by PCR to verify the correct integration. Primer BB118 primes in the cre gene, wheras the other primer (117 or 140 primes upstream of the homology region used. For some case a third primer was used that would give a product from the wt gene before recombination. This PCR fragment will disappear upon correct integration D. P1 Transduction P1 lysates were prepared by diluting 100 µl of a bacterial ON culture into 10 ml LB/5 mM CaCl$_2$/0.2% glucose. After 1 hour shaking at 37° C. 200 µl of a P1 phage lysate was added. Typically, cells lyse after 2-3 more hours. A few drops of Chloroform were added and vortexed to complete lysis and the supernatant was stored at 4° C.

For transduction into a recipient strain 2 ml of a fresh ON culture were spun down and resuspended in 2 ml MC Buffer (0.1M MgSO4, 0.005M CaCl$_2$). 400 µl of cells in MC buffer were incubated for 15 minutes at 37° C. with 400 µl of different dilution of P1 lysate (typically 1:1, 1:5, and 1:50 dilutions). Cells were spun down and resuspended in 800 µl citrate buffer (0.1M, pH 5.5: 9.6 g citric acid, 4.4 g NaOH, dH$_2$O to 500 ml; adjust pH to 5.5 with 10N NaOH, autoclave). 100 µl were spread on Cam selective plates and incubated ON at 37° C.

E. Recombination and Subsequent Removal of Markers and Plasmids

Recombination and Subsequent Removal of Markers and Plasmids

Competent cells were prepared for recombination by transfection of pKD46 into BW25223 and DH10B-derived strains were recovered in 1 ml NZY for 1 hour at 37° C. before plating 10 to 200 µl on CAM selective plates.

The Cam selection marker was cleared by transformation of the strain with a Flp recombinase expression plasmid pACYC-Flp-Gent and selection with 15 ug/ml Gentamycin at 30° C. Pooled colonies were replated and individual colonies were screened for loss of Cam-resistance. The pACYC-Flp-Gent plasmid was determined very stable in all strains, but could be bounced out by transformation with plasmid pLys upon selection for Cam-resistance. The pLys plasmid is lost spontaneously if not selected for the Cam-resistance marker. Again, individual colonies were patched to screen for loss of Cam (pLysS), Gentamycin (pACYC-Flp-Gent), and Ampicillin (pKD46 or 46I). Colonies sensitive to all 3 marker needed to be screened for the absence of extrachromosomal DNA by a miniprep extraction (Note: One clone, Sure 3.2.5.8, was found to contain extrachromosomal DNA, although it was sensitive to all three antibiotics.)

F. Preparation of Chemically Competent cells

Sure Strains:

100 ml NZY were inoculated with 1 ml fresh overnight (ON) culture and grown to an optical density (O.D.600) of ~0.25 in the shaker at 37° C. For induction of the Cre recombinase, 1 ml of 1 M L-Arabinose was added and incubation continued for about 20 minutes, at which point the OD600 reached ~0.35. The broth was cooled on ice and pelleted at 3500 rpm at 4° C. The supernatant was discarded and the cell pellet was resuspended in 20 ml ice-cold FSB/Glycerol and kept on ice for 20 minutes. Cells were spun again and the pellet was resuspended in 4 ml FSB/10% glycerol/7%DMSO.

DH10B Strains:

100 ml LB/20 mM MgSO$_4$ were inoculated with 1 ml fresh ON culture, Cells were grown at 37° C. to OD600 of about 0.4. For induction of cre and or the recBC inhibitor, 1 ml of 1M L-Arabinose was added and incubation continued for 20 minutes. Broth was cooled on ice, pelleted at 3500 rpm at 4° C. Cell pellet was resuspended in 20 ml ice-cold PG buffer (30 mM KC$_2$H$_3$O$_2$ pH 5.8, 10 mM CaCl$_2$, 50 mM MnCl$_2$, 100 mM RbCl and 15% glycerol) and kept on ice for 5 minutes. Cells were spun again and the pellet was resuspended 2 ml ice-cold MG buffer (10 mM MOPS pH 6.5, 75 mM CaCl$_2$, 10 mM RbCl and 15% glycerol). Cells are aliquoted and kept on ice for a total of 60 min and frozen at −80° C.

Example 10

Construction of the L-Arabinose-Inducible Cre Strain.

The arabinose operon was chosen for the controlled expression of cre-recombinase. Expression of the B, A, and D genes of the ara operon is tightly controlled by the product of the araC gene, and induction is strictly dependent on the presence of arabinose (Lee et al, 1987). In order to generate an integrated ara-cre expression cassette, the araBAD genes were replaced with cre recombinase by recombination. This technology utilizes the λ red gam recombination system to target chromosomal integration by homologous recombination. The integration occurs precisely at a site predetermined by the flanking sequences of the integration insert. A 30 base pair region of homology is sufficient to target integration (Datsenko and Wanner, 2000). Integration events are typically selected for by a selection marker present on the inserted fragment, which can subsequently be removed if it is flanked by appropriate sites permitting site specific recombination.

Figure 15:
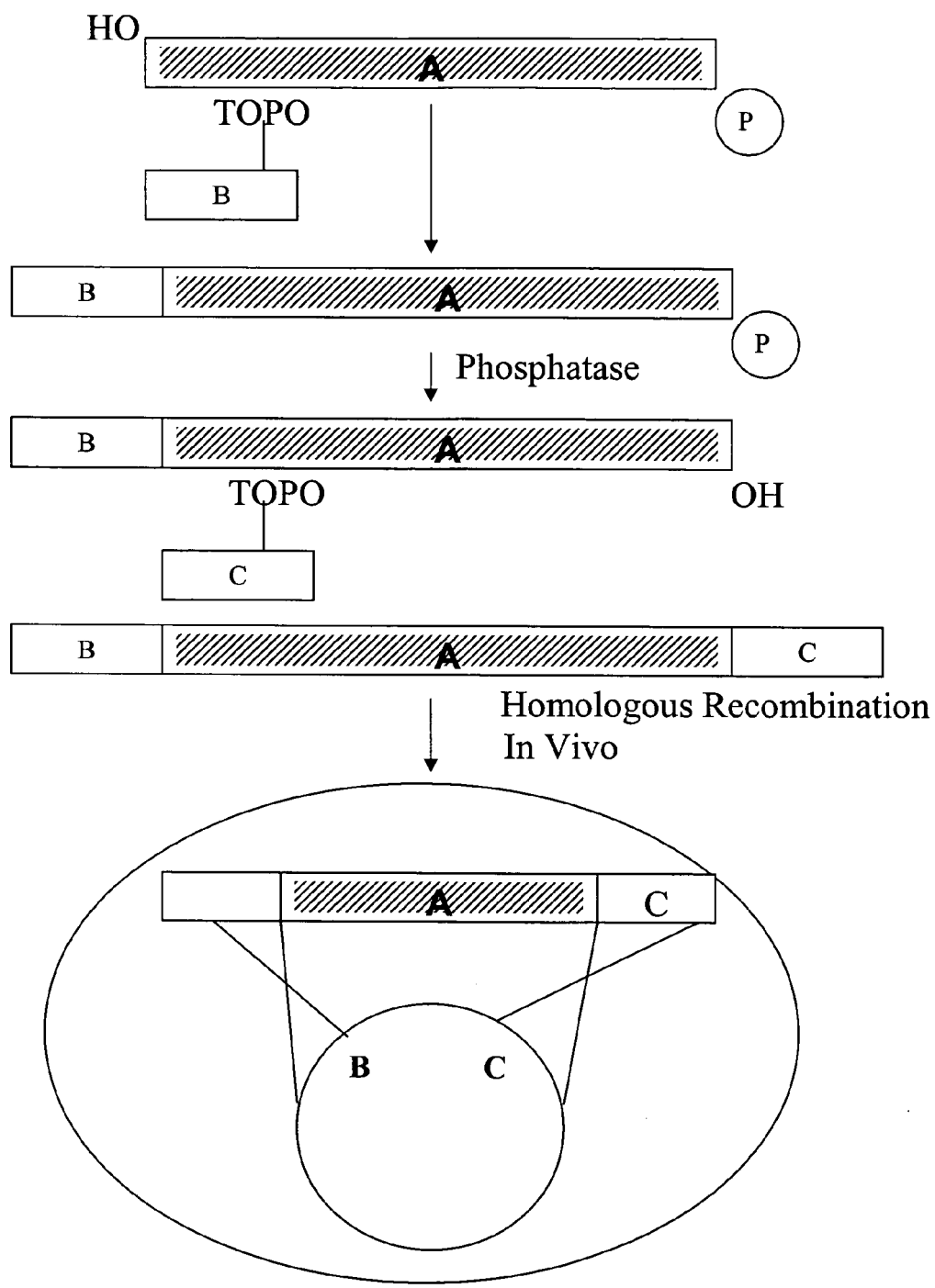
FIG. 15 shows the directional cloning of an insert molecule with a 5'—OH group on one end and a 5'-phosphate group on the other end to vector molecules comprising a topoisomerase polypeptide on one end only and a cloning substrate site, a site for homologous recombination, on the other end.

The overall strategy used for assembly of a PCR cassette for recombination is described in FIG. 15. The cre recombinase was inserted in place of the araA and araB genes. In addition, the ribosomal binding site (RBS) was modified by deletion of one T 12 bp upstream of the ATG start codon. This results in a consensus ribosome binding site (AGGAG) 7 bp upstream of the translational start site. A chloramphenicol selection marker (Cam) was placed downstream of the cre gene to be able to select for recombination events. The Cam$^R$ gene was flanked by FRT sites to be able to remove the selection marker by consecutive Flp recombinase expression.

Figure 16:
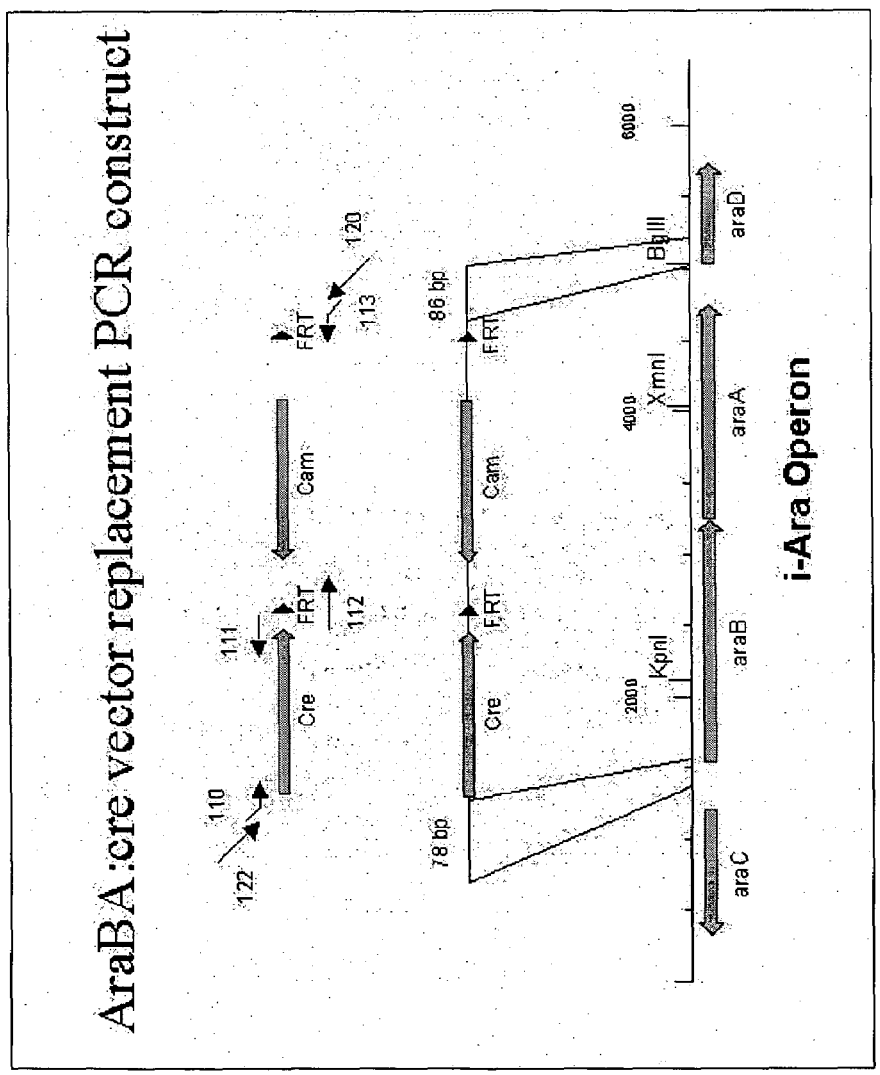
FIG. 16 shows a strategy of assembly of the targeting vector using overlap extension PCR and the Ara operon site that is targeted for recombination. Reamplification with the outer primers results in 78 and 86 bp homology regions for recombination.
Figure 17:
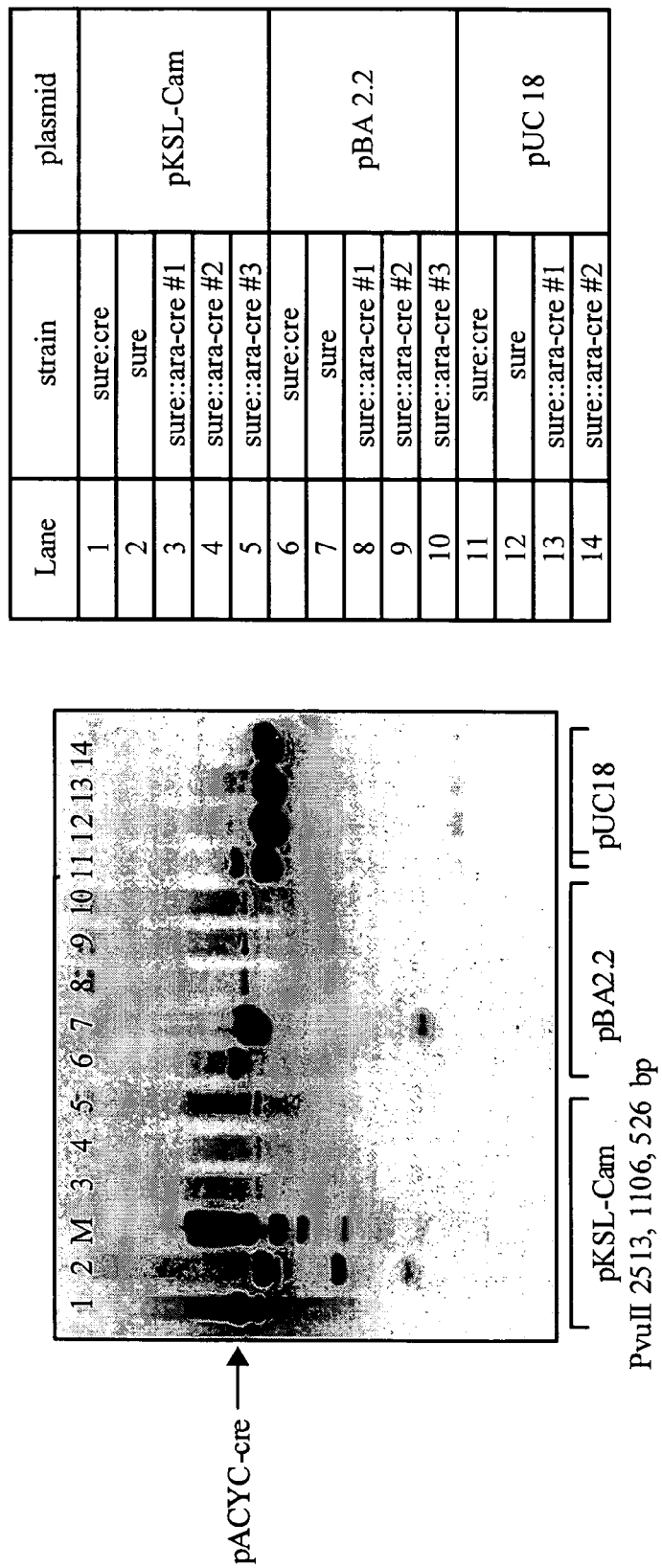
FIG. 17 shows inefficient isolation of loxP-containing plasmid DNA from cells that express high levels of cre recombinase. LoxP containing tester plasmids pKSL-Cam and pBA2.2 and the control plasmid pUC18 (no loxP) were introduced into Sure, Sure:cre (with pACYC-cre) or clones sure:ara-cre #1 to 3 of Sure containing an integration replacement of AraBAD with the cre recombinase gene (see Chapter 3.1). Miniprep DNA was isolated from individual colonies and a 4 ul aliquot was digested with PvuII and separated on a 1% Agarose gel. Unrearranged pKSL-Cam results in fragment s of 2513 bp, 1106 bp and 526 bp in length. After cre mediated deletion of the Cam marker Pvull digestion results in 2513 bp and 413 bp fragments. Assignment of Plasmid DNA and host to the lanes is shown on the insert.

This expression cassette was introduced into the recombination strain BW25113 expressing the λ-red gam genes by electroporation. The resulting Cam-resistant colonies represented the desired integration event as confirmed by PCR using primer annealing within the recombination cassette and outside of the targeted homology region. The resulting araBAD::cre cam$^R$ locus was transferred to Sure by P1 transduction. However, although the resulting strains (Sure:ara-cre#1 and #3) clearly expressed cre-recombinase upon arabinose induction, the cre expression level in the absence of induction were still sufficient to interfere with the purification of LoxP containing plasmids (FIG. 16).

In order to reduce the uninduced cre-expression level two changes were introduced into the promoter fragment. First, the ribosome binding site was reverted from the consensus sequence to the original araB ribosome binding site. In addition, a putative promoter sequence present in cre-recombinase ORF was removed that might give rise to a possibly active cre-derivative lacking the N-terminal 27 amino acids. Changes in the araB promoter cre junction are shown below, with sequence changes highlighted. The ribosome binding site is boxed and the start codon is underlined:

(SEQ ID NO: 3)

Targeting vector 120/122

GGA-GGACGAACATATGTCCAATTTACTGACCGTACACCAAAATTTGCCTGCAT (SEQ ID NO: 4)

V3.0 (putative promoter silenced, wt RBS)

GGATGGAGGAAACGATGTCCAA▓▓T▓CTGACCGTACACCAAAATTTGCCTGCAT

A targeting cassette containing these modifications was integrated in the genome of Sure by performing recombination directly in this strain. Although the derived strains expressed arabinose inducible cre recombinase at apparently lower levels, purification of loxP containing plasmids from this strain was still impaired (data not shown). We therefore attempted to further reduce uninduced cre-expression by changing the translational start codon form AUG to GUG. Replacement of AUG with GUG typically reduces expression level in E. coli about 10-fold.

The recombination cassette containing these additional modifications was integrated into the genome of Sure by direct recombination. All chloramphenicol resistant colonies derived contained the desired integration event as confirmed by PCR. One clone that had spontaneously lost the λ-red/gam expression plasmid pKD46I (Sure 3.2.5) was characterized further.

Figure 18:
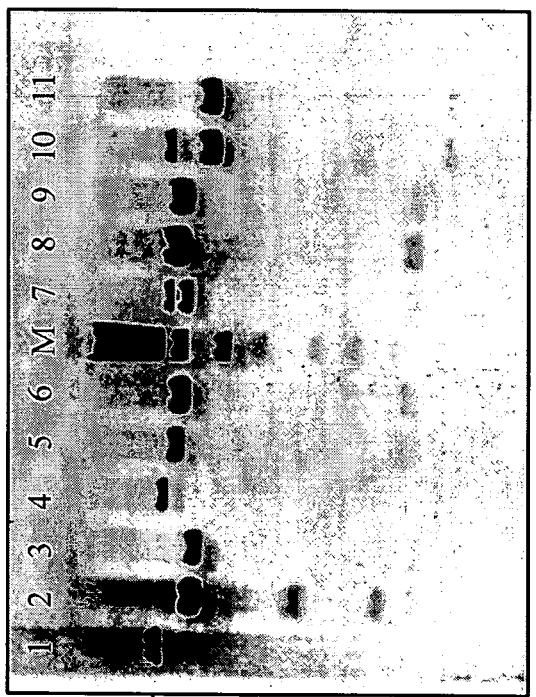
FIG. 18 shows undetectable expression of Cre in uninduced sure 3.2.5 (GTG). PvuII digest of plasmid extracted from Sure:cre (with pACYC-cre), Sure 3.2.5.(ara:cre V3.0 GTG) and R2V4.0 (clone 17 XL10 replacement Gold (ara:cre myc-tagged with AUG start, this clone won't be mentioned further and just served as a control in this experiment). Lane assignment as indicated by the inserted key.

When tested for Cre-expression with the tester plasmid pKSL-cam, no Cre-activity could be detected in uninduced Sure 3.2.5 (FIG. 18) although the strain is proficient for cre activity upon induction (not shown). The tester plasmid pKSL-cam contains the chloramphenicol resistance marker flanked by two LoxP sites. Cre-mediated recombination results in the loss of the loxP-flanked segment. Consistent with this result, LoxP containing plasmids (pKSL-cam and pBA3.3) could be isolated with yields comparable to the control plasmid pUC18.

The chloramphenicol resistance marker of Sure 3.2.5 was removed by FLP mediated recombination, resulting in two independent isolates (Sure 3.2.5.8 and 3.2.5.66.).

Example 11

Stability of Lox-Containing Plasmids in the Cre-Inducible Sure 3.2.5 Strain

Maintenance of loxP site containing plasmids in a cre-expressing host is known to induce deletions involving the loxP site. In order to evaluate the stability of a loxP containing plasmid in Sure cells, two β-galactosidase expressing plasmids (PCH110 and pCAD-βgal-BT) were introduced into the following strains:
  Sure-1 (Stratagene),
  Sure 3.2.5.66 where cre had been induced for 30 min before the cells were made competent, and
  the Sure:cre strain that constitutively expresses cre from the pACYC-cre plasmid.

The tester plasmids contain the full length β-galactosidase open reading frame (3.7 kb) with either no LoxP sites (pCH110) or a loxP immediately 5' to the ORF (pCAD-βgal-BT). Deletions involving the β-gal ORF result in white colonies when the host cells are plated on x-gal plates. The control vector CH110 (no loxP site) did not give rise to white colonies in any of the host cells. In contrast, pCAD-βgal-BT transformed into the Sure:cre strain resulted in the appearance of white colonies in with an average frequency of 6.7% (Table 1). No white colonies were observed with this vector in conventional Sure cells, demonstrating the cre-dependence of the deletion events. Using the same tester construct only one white colony was observed in one experiment in strain Sure 3.2.5.66, corresponding to a 24-fold improvement of stability compared to Sure:cre.

TABLE 1

Stability of loxP containing plasmids is improved in Sure 3.2.5.66

|  |  | CH110 | | CAD-β gal-BT | |
| --- | --- | --- | --- | --- | --- |
| sample | strain | white | blue | white | blue |
| Exp. 1 | sure:cre | 0 | 300 | 14 | 200 |
|  | sure | 0 | 300 | 0 | 163 |
|  | sure 3.2.5.66 | 0 | 400 | 1 | 150 |
| Exp. 2 | sure:cre | 0 | 260 | 8 | 128 |
|  | sure | 0 | 200 | 0 | 200 |
|  | sure 3.2.5.66 | 0 | 170 | 0 | 200 |

Table 6: Plasmids CH110 and CAD-βGal-BT were diluted and transformed into Sure, sure:cre and Sure 3.2.5.66. Transformation was plated on Amp with X-Gal and IPTG. Plates were analyzed for wild type blue and mutant white colonies after ON at 37° C.

Example 12

DH10B-Derived Strain for Circularizing the Linear Topoisomerase Vectors

Nuclease activity by a functional RecBCD enzyme is expected to reduce the overall circularization efficiency as the nuclease would destroy the linear DNA molecule prior to circularization. However, RecBCD positive cells may have additional advantages, including generally faster dividing times, and ability to incorporate a recA mutation without compromising cell stability. Therefore, the following experiments were performed in order to determine whether a RecBCD positive cell.

First, the ara::cre cassette was transferred from Sure 3.2.5.66 cells by P1 transduction into DH10B This strain is F- and recA, readily produces blue and white colonies by α-complementation. It can be made competent very efficiently and forms large colonies after 16 hours at 37° C. After P1 transduction, the cam marker was removed by Flp mediated recombination, resulting in the strain DH10B-812. This strain was made chemically competent using the TFB method after induction of Cre expression with arabinose and compared to Sure 3.2.5.8 cells in the efficiency of cloning the 1.8 kb Cam-OFP test insert in pBA 3.3 Topoisomerase-charged vector. As shown in Table 2, DH10B-812 was comparable to Sure 3.2.5.8 as a recipient strain for Topo cloning. This is likely due to the superior transformation efficiency of DH10B-812, which was almost 10-fold higher than the efficiency of Sure 3.2.5.8. When normalized for transformation efficiency, Sure 3.2.5.8 was about 6-fold more effective than DH10B-812 establishing colonies from linear Topo ligation product. This is consistent with the lack of exonuclease activity in the Sure strains.

TABLE 7

Normalized cloning efficiency for the DH10B:cre is lower than Sure 3.2.5.8

| host | 5 ul Amp/X-gal/IPTG | | | 50 ul Amp/X-gal/IPTG | 15 ul pUC 19 | Transformation efficiency | average ratio OFP over pUC per 300 ul |
| --- | --- | --- | --- | --- | --- | --- | --- |
|  | OFP | white | blue | blue | (0.5 pg) | per 1 ug | transformation |
| DH10B:cre 812 | 81 | 0 | 0 | 6 | 226 | 4.21E+08 | 1.25 |
|  | 95 | 2 | 0 | 5 | 195 |  |  |
| Sure 3.2.5.8 | 61 | 2 | 0 | 3 | 34 | 4.60E+07 | 7.50 |
|  | 54 | 1 | 0 | 2 | 12 |  |  |

Table2: 10 ng of 1.8 kb Cam-OFP test insert was ligated to 1 ul of pBA 3.3 and 2 μl of the ligation reaction (33%) was used to-transform the indicated strains. The indicated volume (out of 300 μl) was plated on Ampicillin plates supplemented with X-Gal and IPTG. 10 pg of pUC19 served as transformation control. The rightmost column displays the number of insert-containing (OFP+) colonies per number of pUC transformants.

Example 13

DH10 Strain for Circularizing the Linear Topo Vector with a recBC Inhibitor

Based on the results above, it can be projected that high efficiency cloning strains like DH10B containing a recBC mutation would be more effective host strains for linear topo-ligation products. However, E. coli with mutations in recABC are very unstable, presumably because DNA breaks cannot be repaired. An alternative approach was attempted in which transient repression RecBCD activity was achieved, generated by transiently expressing inhibitors of recBC in a recA host. The recBC inhibitor from the T3-phage (gene 5.9) and the λ-gam gene were introduced into the ara-cre expression cassette, in effect generating an arabinose inducible cre/recBC inhibitor operon. In the first attempt, the recBC inhibitors were inserted 3' to the cre recombinase. However, these strains did not result in improved circularization efficiency (not shown). In contrast, in case of the λ-gam gene, reversing the order of recBC inhibitor and cre recombinase (DH10B: ara-gam-cre20; F-mcrA Δ(mrr-hsdRMS-mcrBC) φ80dlacZΔM15 ΔlacX74 deoR recA1 endA1 ΔaraBAD:: λgam-Plcre galU galK rpsL nupGλk-tonA) resulted in a dramatic improvement in circularization efficiency (not shown). The resulting strain, DH10B:ara-gam-cre, was as efficient as Sure 3.2.5.8 with regard to the efficiency to establish a colony from a linear Topo ligation product.

We claim:

1. An isolated *Escherichia coli* cell comprising an integrated expression construct, wherein the integrated expression construct comprises 1) a Cre recombinase gene, 2) a gene encoding an inhibitor of RecBCD, wherein the RecBCD inhibitor is a lambda Gam, a T3 gene, a 5.9 protein, or a P22 Abc2 protein, and 3) an inducible promoter that is operably linked to the Cre recombinase gene and the gene encoding the RecBCD inhibitor.

2. The cell of claim 1, which is competent.

3. The cell of claim 2, wherein said Cre recombinase and RecBCD inhibitor are transiently expressed by a process comprising: treating said cell to induce expression of said Cre recombinase and RecBCD inhibitor prior to making said cells competent.

4. The cell of claim 1, wherein the inducible promoter is an arabinose-inducible promoter.

5. A method of circularizing a linear DNA molecule comprising at least two loxP sites, comprising introducing said DNA into said cells of claim 1, wherein said linear DNA molecule is joined at said loxP sites.

6. The method of claim 5, wherein said cell lacks a functional recB gene.

7. The method of claim 5, wherein said cell lacks a functional recC gene.

8. The method of claim 5, wherein said RecBCD activity of said cell is transiently repressed.

9. The method of claim 5, wherein said cell inducibly expresses an inhibitor of RecBCD selected from the group consisting of lambda Gam, T3 gene 5.9 protein, and P22 Abc2 protein.

10. The method of claim 5, wherein said cell inducibly expresses said Cre recombinase protein.

11. The method of claim 5, wherein said cell is competent.

12. The cell of claim 11, wherein said Cre recombinase is transiently expressed by a process comprising: treating said cell to induce expression of said Cre recombinase prior to making said cells competent.

13. The cell of claim 4, further comprising one or more mutations in the arabinose-inducible promoter region or the Cre recombinase gene, wherein the one or more mutations reduce basal levels of Cre recombinase expression.

14. The cell of claim 13, wherein the start codon of the Cre recombinase gene is mutated from an ATG to a GTG.

15. The cell of claim 14, wherein a putative promoter sequence in the Cre recombinase gene is mutated.

16. The cell of claim 15, wherein the putative promoter sequence is located at about 6-9 nucleotides downstream of the Cre recombinase start codon.

17. The cell of claim 16, wherein the ribosome binding site of the arabinose-inducible promoter region is mutated.

18. The cell of claim 13, wherein the RecBCD inhibitor is lambda Gam.

* * * * *

UNITED STATES PATENT AND TRADEMARK OFFICE
CERTIFICATE OF CORRECTION

PATENT NO. : 7,517,688 B2 Page 1 of 1
APPLICATION NO. : 11/284343
DATED : April 14, 2009
INVENTOR(S) : Joseph A. Sorge et al.

It is certified that error appears in the above-identified patent and that said Letters Patent is hereby corrected as shown below:

On the Title page, in field (57), under "Abstract", in column 2, line 9, delete "loxp" and insert -- loxP --, therefor.

Signed and Sealed this

Fourteenth Day of July, 2009

JOHN DOLL
*Acting Director of the United States Patent and Trademark Office*

SEQUENCE LISTING

<160> NUMBER OF SEQ ID NOS: 4

<210> SEQ ID NO 1
<211> LENGTH: 6
<212> TYPE: DNA
<213> ORGANISM: Vaccinia virus

<400> SEQUENCE: 1 ctcctt                                                                    6

<210> SEQ ID NO 2
<211> LENGTH: 34
<212> TYPE: DNA
<213> ORGANISM: Artificial sequence
<220> FEATURE:
<223> OTHER INFORMATION: LoxP site consensus sequence

<400> SEQUENCE: 2
ataacttcgt ataatgtatg ctatacgaag ttat                                     34

<210> SEQ ID NO 3
<211> LENGTH: 53
<212> TYPE: DNA
<213> ORGANISM: Artificial sequence
<220> FEATURE:
<223> OTHER INFORMATION: AraB promoter Cre junction

<400> SEQUENCE: 3
ggaggaggaa catatgtcca atttactgac cgtacaccaa aatttgcctg cat                53

<210> SEQ ID NO 4
<211> LENGTH: 54
<212> TYPE: DNA
<213> ORGANISM: Artificial sequence
<220> FEATURE:
<223> OTHER INFORMATION: Modified araB promoter Cre junction

<400> SEQUENCE: 4
ggatggagga aacgatgtcc aacctgctga ccgtacacca aaatttgcct gcat               54